US010689634B2

(12) United States Patent
Thompson et al.

(10) Patent No.: US 10,689,634 B2
(45) Date of Patent: *Jun. 23, 2020

(54) METHODS OF COMBINED BIOPROCESSING AND RELATED MICROORGANISMS, THERMOPHILIC AND/OR ACIDOPHILIC ENZYMES, AND NUCLEIC ACIDS ENCODING SAID ENZYMES

(71) Applicant: Battelle Energy Alliance, LLC, Idaho Falls, ID (US)

(72) Inventors: David N. Thompson, Idaho Falls, ID (US); William A. Apel, Jackson, WY (US); Vicki S. Thompson, Idaho Falls, ID (US); Thomas E. Ward, PA Furnace, PA (US)

(73) Assignee: Battelle Energy Alliance LLC, Idaho Falls, ID (US)

(*) Notice: Subject to any disclaimer, the term of this patent is extended or adjusted under 35 U.S.C. 154(b) by 0 days.

This patent is subject to a terminal disclaimer.

(21) Appl. No.: 16/511,133

(22) Filed: Jul. 15, 2019

(65) Prior Publication Data

US 2019/0345468 A1 Nov. 14, 2019

Related U.S. Application Data

(60) Continuation of application No. 15/676,484, filed on Aug. 14, 2017, now Pat. No. 10,351,835, which is a continuation of application No. 15/074,297, filed on Mar. 18, 2016, now Pat. No. 9,732,330, which is a continuation-in-part of application No. 14/185,501, filed on Feb. 20, 2014, now Pat. No. 9,290,784, which is a continuation-in-part of application No. 13/924,149, filed on Jun. 21, 2013, now Pat. No. 8,691,525, which is a division of application No. 12/587,229, filed on Oct. 2, 2009, now Pat. No. 8,492,114, which is a continuation-in-part of application No. 12/322,359, filed on Jan. 29, 2009, (Continued)

(51) Int. Cl.

| | |
|---|---|
| *C12N 9/16* | (2006.01) |
| *C12P 7/00* | (2006.01) |
| *C12P 1/00* | (2006.01) |
| *C12N 9/24* | (2006.01) |
| *C12P 7/14* | (2006.01) |
| *C12P 19/14* | (2006.01) |
| *C12P 19/02* | (2006.01) |
| *C12N 15/52* | (2006.01) |
| *C12P 7/06* | (2006.01) |
| *C12P 7/10* | (2006.01) |

(52) U.S. Cl.
CPC ........... *C12N 9/2402* (2013.01); *C12N 15/52* (2013.01); *C12P 7/065* (2013.01); *C12P 7/10* (2013.01); *C12P 7/14* (2013.01); *C12P 19/02* (2013.01); *C12P 19/14* (2013.01); *C12P 2201/00* (2013.01); *C12Y 302/01139* (2013.01); *Y02E 50/16* (2013.01); *Y02E 50/17* (2013.01)

(58) Field of Classification Search
CPC ... C12N 9/14; C12N 9/16; C12N 9/24; C12N 9/26; C12N 15/52; C12P 19/14; C12P 19/16; C12P 19/34; C07H 21/04; C07K 1/00

See application file for complete search history.

(56) References Cited

U.S. PATENT DOCUMENTS

| | | |
|---|---|---|
| 4,237,226 A | 12/1980 | Grethlein |
| 4,581,333 A | 4/1986 | Kourilsky et al. |
| | (Continued) | |

FOREIGN PATENT DOCUMENTS

| | | |
|---|---|---|
| DE | 19717893 A1 | 1/1999 |
| WO | 8100577 A1 | 3/1981 |
| | (Continued) | |

OTHER PUBLICATIONS

Accession C8WVP7. Nov. 3, 2009.
(Continued)

*Primary Examiner* — Maryam Monshipouri
(74) *Attorney, Agent, or Firm* — Patent Law Works, LLP

(57) ABSTRACT

A genetically modified organism comprising: at least one nucleic acid sequence and/or at least one recombinant nucleic acid isolated from *Alicyclobacillus acidocaldarius* and encoding a polypeptide involved in at least partially degrading, cleaving, transporting, metabolizing, or removing polysaccharides, cellulose, lignocellulose, hemicellulose, lignin, starch, sugars, sugar oligomers, carbohydrates, complex carbohydrates, chitin, heteroxylans, glycosides, xylan-, glucan-, galactan-, or mannan-decorating groups; and at least one nucleic acid sequence and/or at least one recombinant nucleic acid encoding a polypeptide involved in fermenting sugar molecules to a product. Additionally, enzymatic and/or proteinaceous extracts may be isolated from one or more genetically modified organisms. The extracts are utilized to convert biomass into a product. Further provided are methods of converting biomass into products comprising: placing the genetically modified organism and/or enzymatic extracts thereof in fluid contact with polysaccharides, cellulose, lignocellulose, hemicellulose, lignin, starch, sugars, sugar oligomers, carbohydrates, complex carbohydrates, chitin, heteroxylans, glycosides, and/or xylan-, glucan-, galactan-, or mannan-decorating groups.

14 Claims, 5 Drawing Sheets

Specification includes a Sequence Listing.

Related U.S. Application Data now Pat. No. 7,858,353, and a continuation-in-part of application No. 12/380,551, filed on Feb. 26, 2009, now Pat. No. 8,728,803, and a continuation-in-part of application No. 12/380,450, filed on Feb. 26, 2009, now Pat. No. 9,234,228, and a continuation-in-part of application No. 12/380,554, filed on Feb. 26, 2009, now Pat. No. 7,960,534, and a continuation-in-part of application No. 12/380,008, filed on Feb. 20, 2009, now Pat. No. 8,716,011, and a continuation-in-part of application No. 12/321,636, filed on Jan. 23, 2009, now Pat. No. 7,923,234.

(60) Provisional application No. 61/025,136, filed on Jan. 31, 2008, provisional application No. 61/032,339, filed on Feb. 28, 2008, provisional application No. 61/031,984, filed on Feb. 27, 2008, provisional application No. 61/031,593, filed on Feb. 26, 2008, provisional application No. 61/030,820, filed on Feb. 22, 2008, provisional application No. 61/023,639, filed on Jan. 25, 2008.

(56) References Cited

U.S. PATENT DOCUMENTS

| | | | |
|---|---|---|---|
| 4,624,922 | A | 11/1986 | Horikoshi et al. |
| 5,098,825 | A | 3/1992 | Tchen et al. |
| 5,643,758 | A | 7/1997 | Guan et al. |
| 5,882,905 | A | 3/1999 | Saha et al. |
| 5,916,795 | A | 6/1999 | Fukunaga et al. |
| 5,948,667 | A | 9/1999 | Cheng et al. |
| 6,083,733 | A | 7/2000 | Gronberg et al. |
| 6,268,197 | B1 | 7/2001 | Schulein et al. |
| 6,426,211 | B1 | 7/2002 | de Buyl et al. |
| 6,506,585 | B2 | 1/2003 | Danielsen et al. |
| 6,777,212 | B2 | 8/2004 | Asakura et al. |
| 6,833,259 | B2 | 12/2004 | Bhosle et al. |
| 7,727,755 | B2 | 6/2010 | Thompson et al. |
| 7,858,353 | B2 * | 12/2010 | Thompson .............. C12N 15/52 435/18 |
| 7,923,234 | B2 | 4/2011 | Thompson et al. |
| 7,960,534 | B2 | 6/2011 | Thompson et al. |
| 8,071,748 | B2 | 12/2011 | Thompson et al. |
| 8,202,716 | B2 | 6/2012 | Thompson et al. |
| 8,298,799 | B2 | 10/2012 | Bornscheuer et al. |
| 8,431,379 | B2 | 4/2013 | Thompson et al. |
| 8,492,114 | B2 | 7/2013 | Thompson et al. |
| 9,222,094 | B2 | 12/2015 | Thompson et al. |
| 9,404,134 | B2 * | 8/2016 | Thompson ............ C12N 9/1051 |
| 9,499,824 | B2 | 11/2016 | Lee et al. |
| 9,879,247 | B2 | 1/2018 | Thompson et al. |
| 2003/0134395 | A1 | 7/2003 | Shetty et al. |
| 2003/0233674 | A1 | 12/2003 | Gabor et al. |
| 2003/0233675 | A1 | 12/2003 | Cao et al. |
| 2004/0029129 | A1 | 2/2004 | Wang et al. |
| 2005/0112742 | A1 | 5/2005 | Thompson et al. |
| 2005/0112774 | A1 | 5/2005 | Gilbert et al. |
| 2006/0105442 | A1 | 5/2006 | Wu et al. |
| 2006/0211083 | A1 | 9/2006 | Katzen et al. |
| 2007/0082381 | A1 | 4/2007 | Wilting et al. |
| 2007/0099282 | A1 | 5/2007 | Thompson et al. |
| 2007/0134778 | A1 | 6/2007 | Benning et al. |
| 2007/0148728 | A1 | 6/2007 | Johnson et al. |
| 2009/0203107 | A1 | 8/2009 | Thompson et al. |
| 2009/0215168 | A1 | 8/2009 | Lee et al. |
| 2009/0221049 | A1 | 9/2009 | Shaw et al. |
| 2009/0226978 | A1 | 9/2009 | Thompson et al. |
| 2009/0253205 | A1 | 10/2009 | Thompson et al. |
| 2009/0263859 | A1 | 10/2009 | Thompson et al. |
| 2009/0269827 | A1 | 10/2009 | Thompson et al. |
| 2010/0203583 | A1 | 8/2010 | Thompson et al. |
| 2010/0311110 | A1 | 12/2010 | Thompson et al. |
| 2011/0081683 | A1 | 4/2011 | Thompson et al. |
| 2011/0250683 | A1 | 10/2011 | Thompson et al. |
| 2011/0275135 | A1 | 11/2011 | Lee et al. |
| 2012/0015407 | A1 | 1/2012 | Thompson et al. |
| 2016/0046911 | A1 | 2/2016 | Thompson et al. |

FOREIGN PATENT DOCUMENTS

| | | |
|---|---|---|
| WO | 9906584 A1 | 2/1999 |
| WO | 2003068926 | 8/2003 |
| WO | 2005066339 A2 | 7/2005 |
| WO | 2006117247 A1 | 11/2006 |
| WO | 2010014976 A2 | 2/2010 |

OTHER PUBLICATIONS

Aden et al., "Lignocellulosic Biomass to Ethanol Process Design and Economics Utilizing Co-Current Dilute Acid Prehydrolysis and Enzymatic Hydrolysis for Corn Stover," NREL/TP-510-32438, National Renewable Energy Laboratory, Golden Colorado. Jun. 2002, pp. 1-88.

Auerbach et al.. "Lactate dehydrogenase from the hyperthermophilic bacterium *Thermotoga maritima*: the crystal structure at 2.1 A resolution reveals strategies for intrinsic protein stabilization," Structure (London, England:1993) 1998; 6(6):769-81.

Avella et al., "A New Class of Biodegradable Materials: Poly-3-hydroxy-butyrate/Steam Exploded Straw Fiber Composites. I. Thermal and Impact Behaviour," Journal of Applied Polymer Science, vol. 49, 2091-2103 (1993).

Badger, P.C., "Ethanol from cellulose: A general review," In: J. Janick and A. Whipkey (eds.), Trands in new crops and new uses. ASHS Press, Alexandria, VA, 2002, pp. 17-21.

Bailey et al., "Interlaboratory testing of methods for assay of xylanase activity," Journal of Biotechnology, 23 (1992) 257-270.

Barany, F., 1991, PNAS. USA, 88: 189-193.

Bergquist et al., "Molecular diversity of thermophilic cellulolytic and hemicellulolytic bacteria," FEMS Microbiology Ecology 28 (1999) 99-110.

Bertoldo et al., 2004, Eng. Life Sci., 4, No. 6.

Bhatia et al., "Microbial beta-Glucosidases: Cloning, Properties, and Applications," Critical Reviews in Biotechnology, 22(4):375-407, Jan. 1, 2002.

BLAST Search of Seq. ID. 36, accessed Apr. 22, 2009, 54 pages.
BLAST Search of Seq. ID. 456, accessed Apr. 22, 2009, 48 pages.
BLAST Search of Seq. ID. 458, accessed Apr. 22, 2009, 59 pages.
BLAST Search of Seq. ID. 460, accessed Apr. 22, 2009, 37 pages.
BLAST Search of Seq. ID. 462, accessed Apr. 22, 2009, 35 pages.
BLAST Search of Seq. ID. 464, accessed Apr. 22, 2009, 45 pages.

Bork. Peer. "Powers and Pitfalls in Sequence Analysis: The 70% Hurdle." Genome Research, 2000, 10:398-400.

Borman, S., 2006, Glycosylation Engineering. Chem. Eng. News, 84(36): 13-22.

Bowie et al., "Deciphering the Message in Protein Sequences: Tolerance to Amino Acid Substitutions," Science, 1990, 247:1306-1310.

Breves et al., "Genes Encoding Two Different beta-Glucosidases of Thermoanaerobacter brockii are Clustered in a Common Operon," Applied and Environmental Microbiology, vol. 63, No. 10, Oct. 1997, pp. 3902-3910.

Broun et al. "Catalytic Plasticity of Fatty Acid Modification Enzymes Underlying Chemical Diversity of Plant Lipids" Science vol. 282 Nov. 13, 1998 pp. 1315-1317 (4 pages).

Buckholz, R. G., 1993, Yeast systems for the expression of heterologous gene products. Curr. Op. Biotechnology 4: 538-542.

Burg, J. L. et al., 1996, Mol. and Cell. Probes, 10: 257-271.

Chica et al., "Semi-rational approaches to engineering enzyme activity: combining the benefits of directed evolution and rational design", Curr Opin Biotechnol, (Aug. 2005) 16(4): 378-84.

Chu, B. C. F. et al., 1986, NAR, 14: 5591-5603.

Collins et al., "Xylanases, Xylanase Families and Extremophilic Xylanses," FEMS Microbiology Review, 2005, pp. 3-23.

(56) References Cited

OTHER PUBLICATIONS

Cowling, Ellis B., "Physical and Chemical Constrains in the Hydrolysis of Cellulose and Lignocellulosic Materials," Biotechnol. Bioeng. Symposium No. 5, 163-181 (1975).
Crout et al., "Glycosidases and glycosyl transferases in glycoside and oligosaccharide synthesis," Current Opinion in Chemical Biology, Current Biology LTD, London, GB, vol. 2, No. 1, Feb. 1, 1998, pp. 98-111.
Dale, M. Clark, "Enzymatic simultaneous saccharification and fermentation (SSF) of biomass to ethanol in a pilot 130 liter multistage continuous reactor separator," Bio-Process Innovation, Inc., W. Lafayette, IN, 2005, 10 pages.
Database EMBL [Online]. Mar. 16, 2007. XP-002627757. Database accession No. ER073884, 1 page.
Database Geneseq [Online]. May 21, 1998. XP-002627734. Database accession No. AAW35004, 1 page.
Database SCORE [Online]. Feb. 10, 2009. Database accession No. B7DQJ6, 2 pages.
Database SCORE [Online]. Nov. 3, 2009. Database accession No. C8WYA8, 2 pages.
Database UniProt [Online]. May 1, 1997. XP-002630045. Database accession No. P96090, 1 page.
Database UniProt [Online]. Oct. 1, 2001. XP-002627736. Database accession No. Q97U14, 1 page.
Database UniProt [Online]. Feb. 10, 2009. XP-000002659383. Database accession No. B7DT70, 1 page.
Database UniProt [Online]. Feb. 10, 2009. XP-002674095. Database accession No. B7DM51. 1 page.
Database UniProt [Online]. Feb. 10, 2009. XP-002695727. Database accession No. B7DUZ1, 1 page.
Database UniProt [Online]. Feb. 10, 2009. XP-002698982. Database accession No. B7DRM6, 1 page.
Database UniProt [Online]. Jun. 26, 2007. XP-002627735. Database accession No. A51KZ4, 1 page.
Database Uniprot [Online]. Nov. 3, 2009. Database accession No. C8WVZ2, 2 pages.
Database UniProt [Online]. Nov. 3, 2009. XP-002627733. Database accession No. C8WTP2, 1 page.
Devos et al. "Practical Limits of Functiona Prediction" Proteins: Structure, Function, and Genetics 41 (2000) pp. 98-107 (10 pages).
DiLauro et al., "Characterization of a p-glycosidase from the thermoacidophilic bacterium *Alicyclobacillus acidocaldarius*", Extremophiles (2006) 10:301-310.
Doan et al., "Regulation of the central glycolytic genes in Bacillus subtilis: binding of the repressor CggR to its single DNA target sequence is modulated by fructos-1,6-bisphosphate", Molecular Microbiology, 47(6), 2003, pp. 1709-1721.
Duck, P. et al., 1990, Biotechniques, 9: 142-147.
Eckert et al., "A Thermoacidophilic Endoglucanase (CelB), etc.," Eur. J. Biochem. 270, 2003, pp. 3593-3602.
Eckert et al., "Gene cloning, sequencing, and characterization of a family 9 endoglucanase (CelA) with an unusual pattern of activity from the theremoacidophile Alicyclobacillus acidocaldarius ATCC27009," Applied Microbiology and Biotechnology, vol. 60, No. 4, Dec. 2002, pp. 428-436.
Eckert, Kelvin, "Dissertation, Cloning and Characterization of two glycosidases from the acidothermophile Alicyclobacillus acidocaldarius ATCC27009," Berlin, Dec. 18, 1971, 113 pages.
EC-PDB Database, EC 3.2.1.21 Beta Glucosidase, Hydrolysis of terminal, non-reducing beta-D-Giucosyl Residues with release of Beta-D-glucose, www.ebi.ac.uklthornton-srv/databases/cgi-bin/enzymes/GetPage. plec_number=3.2.1.21, accessed Jan. 28, 2012.
Ito et al., "Purification and properties of acid stable xylanases from Aspergillus kawachii," Bioscience Biotechnology and Biochemistry 56 (4):547-550, Apr. 1992.
Iwata et al., "T and R states in the crystals of bacterial L-lactate dehydrogenase reveal the mechanism for allosteric control," Nature Structural Biology 1, 176-185 (1994).
Jeffries, 1996, Curr. Op. in Biotech., 7:337-342.

Jones et al., "Cloning and transcriptional analysis of the Thermoanaerobacter ethanolicus strain 39E maltose ABC transport system," Extremophiles 2002, 6:291-299.
Keller et al., "Microbial Pretreatment of Biomass: Potential for Reducing the Severity of Thermochemical Biomass Pretreatment," Applied Biochemistry and Biotechnology, vol. 105-108, 2003.
Kenealy et al., "Rapid 2,2-bicinchoninic-based xylanase assay compatible with high throughput screening," Biotechnology Letters 25: 1619-1623, 2003.
Kievitis, T. et al., 1991, J. Virol. Methods, 35: 273-286.
Knappert et al., "Partial Acid Hydrolysis of Cellulosic Materials as a Pretreatment for Enzymatic Hydrolysis," Biotechnology and Bioengineering, vol. XXII, pp. 1449-1463 (1980).
Kohler, G. et al., 1975, Nature, 256(5517): 495497.
Kulkarni et al., "Molecular and biotechnological aspects of xylanases," FEMS Microbiology Reviews 23 (1999) 411-456.
Kwoh, D. Y. et al., 1989, PNAS. USA, 86: 1173-1177.
Lau et al., "PCR ligation mutagenesis in transformable streptococci: application and efficiency," Journal of Microbiological Methods 49 (2002) 193-205.
Lauro et al., "Isolation and characterization of a new family 42 beta-galactosidase from the thermoacidophilic bacterium *Alicyclobacillus acidocaldarius*: Identification of the active site residues," Biochimica et Biophysica Acta 1784 (2008) 292-301.
Lauro et al.. "Characterization of a-glycosidase from the thermoacidophilic bacterium *Alicyclobacillus acidocaldarius*," Extremophiles (2006) 10:301-310.
Lavarack et al., "The acid hydrolysis of sugarcane begasse hemicellulose to produce xylose, arabinose, glucose and other products," Biomass and Bioenergy 23 (2002) 367-380.
Lee et al., "Oxygen Effects on Thermophilic Microbial Populations in Biofilters Treating Nitric Oxide Containing Off-Gas Streams," Environmental Progress, vol. 20, No. 3, Oct. 2001.
Lin et al., "Purification, Characterization, and Gene Cloning of Thermopsin, a Thermostable Acid Protease from Sulfolobus acidocaldarius," The Journal of Biological Chemistry, 1990, vol. 265, No. 3, pp. 1490-1495.
Liu C, and CE Wyman, 2003, The effect of flow rate of compressed hot water on xylan, lignin, and total mass removal from corn stover, Ind. Eng. Chem. Res., 42:5409-5416.
Lucas et al.. C4-Dicarboxylate Transporter/Malic Acid Transport Protein [Alicyclobacillus acidocaldarius LAA1]. GenBank Direct Submission, Accession No. EED06059, Dec. 17, 2008 (Retrieved from the Internet Dec. 15, 2009: URL:http://www.ncbl.nlm.nlh.gov/protein/218238848), p. 2.
Luckow, V. A., 1993, Baculovirus systems for the expression of human gene products. Curr. Op. Biotechnology 4: 564-572.
Lynd et al., 2002, Micro. and Mol. Biol. Rev., vol. 66, No. 3, p. 506-577.
Lynd, Lee R., "Overview and Evaluation of Fuel Ethanol from Cellulosic Biomass: Technology, Economics, the Environment, and Policy," Annu. Rev. Energy Environ. 1996, 21:403-65.
Mackenzie et al., "Multiple Chromosomes in Bacteria: The Yin and Yang of trp Gene Localization in Rhodobacter sphaeroides 2.4.1," Genetics 153: 525-538 (Oct. 1999).
Malherbe and Cloete, 2002, ReNiew in Environmental Science and Bio/Technology, 1: 105-114.
Manchenko, Gennady P., "Handbook of Detection of Enzymes on Electrophoretic Gels," CRC Press, Inc. 1994, pp. 220-240.
Matthews, J. A. et al., 1988, Anal. Biochem., 169: 1-25.
McCoy, Michael, "Chemical Makers Try Biotech Paths," Chemical Engineering News, Jun. 22, 1998, pp. 13-19.
Merrifield, R. D., 1966, J. Am. Chem. Soc., 88(21): 5051-5052.
Michel et al., "Specificity of the protein secretory apparatus: secretion of the heat-labile enterotoxin B subunit pentamers by different species of Gram bacteria," Gene 152 (1995) pp. 41-45.
Miele, E.A. et al., 1983, J. Mol. Biol., 171: 281-295.
Mielenz, 2001, Curr. Op. in Micro., 4:324-329.
Mosier et al., "Industrial Scale-Up of pH-Controlled Liquid Hot Water Pretreatment of Corn Fiber for Fuel Ethanol Production," Applied Biochemistry and Biotechnology, vol. 125, 2005, pp. 77-97.
Neddleman and Wunsch, J. Mol. Biol. 48: 443 (1970).

(56) References Cited

OTHER PUBLICATIONS

Ng et al., 1981, Applied and Environmental Microbiology, 41(6):1337-1343.
Office Action and Examination Report for Canadian Patent Application No. 2,708,280, dated Jan. 26, 2015, 4 pages.
Office Action and Examination Report for Canadian Patent Application No. 2,712,127, dated Feb. 25, 2015, 8 pages.
Office Action and Examination Report for Canadian Patent Application No. 2,627,334, dated Feb. 2, 2012, 2 pages.
Office Action and Examination Report for Canadian Patent Application No. 2,627,334, dated Oct. 22, 2012, 2 pages.
Office Action and Examination Report for Canadian Patent Application No. 2,708,279, dated Jul. 6, 2015, 4 pages.
Office Action for Chinese Patent Application No. 200680050210.5 dated Feb. 23, 2011, 11 pages.
Office Action for Chinese Patent Application No. 200680050210.5 dated Mar. 28, 2012, 12 pages.
Office Action for Chinese Patent Application No. 200980101404.7 dated Mar. 20, 2012, 7 pages.
Office Action for Chinese Patent Application No. 200980101404.7 dated Aug. 15, 2011, 11 pages.
Office Action for Chinese Patent Application No. 200980106013.4 dated Feb. 14, 2012, 9 pages.
Office Action for Chinese Patent Application No. 200980106043.5 dated Jan. 11, 2013, 7 pages.
Office Action for Chinese Patent Application No. 200980106149.5 dated Apr. 20, 2012, 11 pages.
Office Action for Chinese Patent Application No. 200980107073.8 dated Aug. 3, 2012, 7 pages.
Ohta et al., "Purification and Characterization of an Acidophilic Xylanase from *Aureobasidium pullulans* var. *melanigenum* and Sequence Analysis of the Encoding Gene," Journal of Bioscience and Bioengineering, vol. 92, No. 3, 262-270, 2001.
Olins, P. O., and Lee, S. C., 1993, Recent advances in heterologous gene expression in *E. coli*. Curr. Op. Biotechnology 4: 520-525.
Olive et al., "The Crystal and Molecular Structure of Yeast L-Lactate Dehydrogenase (Cytochrome b2)" Int. J. of Peptide Protein Res, 5:219-228 (1973).
Ooshima et al., "Simultaneous saccharification and fermentation of cellulose: Effect of ethanol on enzymatic saccharification of cellulose," Department of Applied Chemistry, Faculty of Engineering, Osaka City University, Osaka 558, Japan, Jun. 5, 1984.
Pajunen et al.. Microbiology (2005) 151, 1209-1218.
Patel et al., (2006), "Medium and long-term opportunities and risks of the biotechnological production of bulk chemicals from renewable resources: The potential of white biotechnology". The BREW Project. Final Report prepared under the European Commissions GROWTH Programme (DG Research), (publica.fraunhofer.de/eprints/N-48834.pdf).
PCT International Search Report and Written Opinion of the International Search Authority for PCT/US09/32333, dated Jun. 19, 2009, 9 pages.
PCT International Search Report and Written Opinion of the International Search Authority for PCT/US09/35307, dated Jun. 10, 2010, 10 pages.
PCT International Search Report and Written Opinion of the International Search Authority for PCT/US11/34852, dated Oct. 21, 2011, 12 pages.
PCT International Search Report and Written Opinion of the International Searching Authority for PCT/US09/00442, dated May 18, 2009, 8 pages.
PCT International Search Report and Written Opinion of the International Searching Authority for PCT/US09/34701, dated Jan. 12, 2010, 10 pages.
PCT International Search Report and Written Opinion of the International Searching Authority for PCT/US09/35275, dated Feb. 25, 2010, 13 pages.
PCT International Search Report and Written Opinion of the International Searching Authority for PCT/US09/35331. dated Feb. 23, 2010, 10 pages.
PCT International Search Report and Written Opinion of the International Searching Authority for PCT/US10/51095, dated Dec. 2, 2010, 11 pages.
PCT International Search Report of the International Search Authority for PCT/US10/25521 dated Jul. 14, 2010, 10 pgs.
PCT International Search Report of the International Searching Authority for PCT/US06/42566, dated Jul. 25, 2008.
Pearson and Lipman, Proc. Natl. Acad. Sci. (U.S.A.) 85: 2444 (1988).
Perlack et al., "Biomass as Feedstock for a Bioenergy and Bioproducts Industry: The Technical Feasibility of a Billion-Ton Annual Supply," USDA and DOE, Apr. 2005, 78 pages.
Peyton et al., "Biotransformation of Toxic Organic and Inorganic Contaminants by Halophilic Bacteria," Halophilic Microorganisms, Antionio Ventosa (Ed.), Springer, 2004, pp. 315-331.
Ragauskas et al., "The Path Forward for Biofuels and Biomaterials," Science, Jan. 27, 2006, vol. 311, pp. 484-4589.
Ramos et al., "Biomechanical and Biochemical Pulping of Sugarcane Bagasse with Ceriporiopsis subvermispora Fungal and Xylanase Pretreatments," J. Agric. Food Chem. 2001, 49, 1180-1186.
Rezacova et al., "Crystal structures of the effector-binding domain of repressor Central glycolytic gene Regulator from Bacillus subtilis reveal ligand-induced structural changes upon binding of several glycolytic intermediates", Mol Microbial., 69(4): Aug. 2008, pp. 895-910.
Saeman et al., "Quantitative Saccharification of Wood and Cellulose," Industrial and Engineering Chemistry, Jan. 1945, vol. 17, No. 1, pp. 35-37.
Saha et al., "Dilute Acid Pretreatment, Enzymatic Saccharification, and Fermentation of Rice Hulls to Ethanol," Biotechnol. Prag. 2005, 21, 816-822.
Sanchez-Pescador, R., 1988, J. Clin. Microbial., 26(10): 1934-1938.
Sa-Pereira et al., "Rapid production of thermostable cellulose-free xylanase by a strain of Bacillus subtilis and its properties," Enzyme and Microbial Technology, 30 (2002) 924-933.
Schafer et al., "X-ray Structures of the Maltose-Maltodextrin-binding Protein of the Thermoacidophilic Bacterium *Alicyclobacillus acidocaldarius* Provide Insight into Acid Stability of Proteins," J. Mal. Biol. 2004, 335:261-274.
Schaffer, C. et al., 2001, Prokaryotic glycosylation. Proteomics, 1: 248-261.
Scheffel et al., "Functional reconstitution of a maltrose ATP-binding cassette transporter from the thermoacidophilic gram-positive bacterium *Alicyclobacillus acidocaldarius*," Biochem Biophy Acta, 2004, 1656(1):57-65.
Schell et al.. "Dilute-Sulfuric Acid Pretreatment of Corn Stover in Pilot-Scale Reactor." Applied Biochemistry and Biotechnology, vol. 105-108, 2003, pp. 69-85.
Schneider, "Import of solutes by ABC transporters—the maltose system. ABC protein: from bacteria to man," Elsevier Science, London 2003, p. 157-185. [Retrieved from the Internet on Jan. 24, 2010; http://www2.hu-berlin.de/biologie/baktphys/paper/1_ABC/review_chap-09.pdf].
Schwarz. Wolfgang H.. "A list of cellulolytic bacteria," Technische Universitat Munchen, Apr. 24, 2003, 8 pages.
Schwermann, B. et al., 1994, Purification, properties and structural aspects of a thermoacidophilic alpha-amylase from Alicyclobacillus acidocaldarius ATCC 27009, insight into acidostability of proteins. Eur. J. Biochem. 226: 981-991.
Seffernick et al. "Melamine Deaminase and Atrazine Chlorohydrolase: 98 Percent Identical but Functionally Different" Journal of Bacteriology vol. 183, No. 8, Apr. 2001 pp. 2045-2410 (6 pages).
Shallom et al., "Microbial hemicellulases," Current Opinion in Microbiology, Current Biology Ltd, GB, vol. 6, No. 3, Jun. 1, 2003, pp. 219-228.
Simpson et al., "An extremely Thermostable xylanase from the thermophilic eubacterium Thermotoga," Biochem. J. (1991) 277, 413-417.
Singh et al., "Protein Engineering Approaches in the Post-Genomic Era", Curr Protein Pept Sci. (2017) 18, pp. 1-11.
Skolnick et al. (Trends in Biotechnology 18:34-39, 2000).
Smook, GA, "Handbook for Pulp Paper Technologists," Tappi Pr; 2nd Ed. (Jun. 1992) pp. 65-88.

(56) References Cited

OTHER PUBLICATIONS

Somogyi, M., "Notes on Sugar Determination," Journal of Biological Chemistry (1952) pp. 195:19-23.
Subramaniyan et al., "Cellulase-free xylanases from Bacillus and other microorganisms," FEMS Microbiology Letters 183 (2000) 1-7.
Sunna et al., "Glycosyl hydrolases from hyperthermophiles," Extremophiles (1997) 12-13.
Supplemental European Search Report for EP06827231, dated Nov. 11, 2009, 6 pages.
Techapun et al., "Production of a cellulose-free xylanase from agricultural waste materials by a thermotolerant Streptomyces sp.," Biotechnology Letters 23: 1685-1689, 2001.
Thompson et al., "Chapter 31: Changes in the Rate of Enzymatic Hydrolysis and Surface Area Available to Cellulase with Pretreatment Methods," Biotechnology in Pulp and Paper Manufacture: Applications and Fundamental Investigations. Proceedings of the Fourth International Conference on Biotechnology in the Pulp and Paper Industry (ICBPPI), May 16-19, 1989,Raleigh, NC and Myrtle Beach, SC, USA. Kirk, T.K. and Chang, H.M. (eds.). Butterworth-Heinemann, Boston, 1990, pp. 329-338.
Thompson et al., "Comparison of Pretreatment Methods on the Basis of Available Surface Area," Bioresource Technology 39 (1992) 155-163.
Thompson et al., "In Vitro Degradation of Natural Insoluble Lignin in Aqueous Media by the Extracellular Peroxidases of Phanerochaete chrysosporium," 1998 John Wiley Sons, Inc. pp. 704-717.
Thompson et al., "Measurement of fumonsins in corn with a fiber-optic fluoroimmunosensor," SPIE vol. 2980, (2010) pp. 532-538.
Thompson et al., "Preliminary Investigation of Fungal Bioprocessing of Wheat Straw for Production of Straw-Thermoplastic Composites," Applied Biochemistry and Biotechnology, vol. 105-108, 2003, pp. 423-436.
Thompson et al., "Purification and Characterization of a Novel Thermo-Alkali-Stable Catalase from Thermus brockianus," Biotechnol. Prag. 2003, 19, 1292-1299.
Thompson et al., "Thermoacidophilic Cellulases and Hemicellulases from Alicyclobacillus acidocaldarius," Idaho National Laboratory, 2006, 1 page.
Tsao, G.T., "Bacterial Hydrolysis: A Review," Anaerobic Digestion and Carbohydrate Hydrolysis of Waste, Ferrero et al. (eds.), Elsevier Applied Science Publishers, London, 1984, pp. 83-99.
Tsao, GT, MR Ladisch, and HR Bungay, 1987. Biomass Refining, In Advanced Biochemical Engineering, Wiley Interscience, N.Y., 79-101.
EC-PDB Database, EC 3.2.1.37 Xylan 1,4-beta-xylosidase, Hydrolysis of (1-4)-beta-D-xylans, to remove successive D-xylose residues from teh non-reducing termini, www.ebi.ac.uklthornton-srv/databases/cgi-bin/enzymes/GetPage.plec_number=3.2.1.37, accessed Jan. 28, 2012.
EC-PDB Database, EC 3.2.1.55 Alpha-N-arabinofuranosidase, Hydrolysis of terminal non-reducing alpha-L-arabinofuranoside residues in alpha-L-arabinosides, www.ebi.ac. Uklthornton-srv/databases/cgi-bin/enzymes/GetPage.plec_number=3.2.1.55, accessed Jan. 28, 2012.
EC-PDB Database, EC 3.2.1.91 Cellulose 1,4-beta-cellobiosidase (non-reducing end), Hydrolysis of (1-4)-beta-D-glucosidic linkages in cellulose and cellotetraose, releasing cellobiose from the non-reducing ends of the chains, www.ebi.ac.uklthornton-srv/databases/cgi-bin/enzymes/GetPage.plec_number=3.2.1.91, accessed Jan. 28, 2012.
EC-PDB Database. EC 3.2.1.23 Beta Galactosidase. Hydrolysis of terminal non-reducing beta-D-galactose residues in beta-D-galactosides, www.ebi.ac.uklthornton-srv/databases/cgi-bin/enzymes/GetPage.plec_numbers=3.2.1.23, accessed Jan. 28, 2012.
Edwards, C. P., and Aruffo, A., 1993, Current applications of COS cell based transient expression systems. Curr. Op. Biotechnology 4: 558-563.

Ehrman, Tina, "Standard Method for Determination of Total Solids in Biomass," Chemical Analysis and Testing Task, Laboratory Analytical Procedure, Oct. 28, 1994, 242 total pages.
EMBL Submission CP001728, Sep. 2009. [Retrieved from the internet: URL:http://www.ebi.ac.ukTools/dbfetch/embifetchstyle=html id=CP001728 Submit=Go], 51 pages.
Erlich, H.A., J Clin. Immunol., Nov. 1989; 9(6):437-47.
European Office Action for EP 06827231, dated Dec. 7, 2010, 5 pages.
European Office Action for EP 06827231, dated Feb. 7, 2012, 10 pages.
European Office Action for EP 06827231, dated Mar. 2, 2010, 3 pages.
Examination Report for Australian Patent Application No. 2006312031 dated Jun. 1, 2011, 2 pages.
Examination Report for Malaysia Patent Application No. PI 20081221 dated Aug. 30, 2010, 5 pages.
Examination Report for New Zealand Patent Application No. 56777 4 dated Mar. 18, 2010, 2 pages.
Examination Report for New Zealand Patent Application No. 56777 4 dated May 27, 2011, 2 pages.
Examination Report for New Zealand Patent Application No. 585947 dated Feb. 28, 2011, 1 page.
Examination Report for New Zealand Patent Application No. 585950 dated Feb. 24, 2011, 2 pages.
Examination Report for New Zealand Patent Application No. 586498 dated Mar. 1, 2011, 2 pages.
Examination Report for New Zealand Patent Application No. 587062 dated Jul. 18, 2011, 2 pages.
Examination Report for New Zealand Patent Application No. 587062 dated Mar. 8, 2011, 3 pages.
Examination Report for New Zealand Patent Application No. 587185 dated Jun. 21, 2011, 2 pages.
Examination Report for New Zealand Patent Application No. 587188 dated Mar. 8, 2011, 3 pages.
Examination Report for New Zealand Patent Application No. 595377 dated Nov. 7, 2011, 2 pages.
Extended Supplementary European Search Report for EP 09703173, dated Mar. 25, 2011, 7 pages.
Extended Supplementary European Search Report for EP 09703173, dated Apr. 20, 2011, 7 pages.
Extended Supplementary European Search Report for EP 09709191, dated Mar. 29, 2012, 6 pages.
Extended Supplementary European Search Report for EP 09743132, dated Apr. 19, 2013, 4 pages.
Extended Supplementary European Search Report for EP 09755307. dated Apr. 18, 2012, 4 pages.
Extended Supplementary European Search Report for EP 09755308, dated Jun. 18, 2013, 3 pages.
Extended Supplementary European Search Report for EP 09823952, dated Sep. 20, 2011, 7 pages.
Extended Supplementary European Search Report for EP 10746882. dated Aug. 27, 2012, 9 pages.
Fan et al., "The Nature of Lignocellulosics and Their Pretreatments for Enzymatic Hydrolysis," Advances in Biochemical Engineering/Biotechnology, 1982, vol. 23/1982, 157-187.
Fillinger et al., "Two Glyceraldehyde-3-phosphate Dehydrogenases with Opposite Physiological Roles in a Nonphotosynthetic Bacterium", The Journal of Biological Chemistry, vol. 275, No. 19, Issue of May 2000, pp. 14031-14037.
Flanagan, et al., "Development of gas phase bioreactors for the removal of nitrogen oxides from synthetic flue gas streams," Fuel 81 (2002) 1953-1961.
Fushinobu et al., "Crystallographic and mutational analyses of an extremely acidophilic and acid-stable xylanase: biased distribution of acidic residues and importance of Asp37 for catalysis at low pH," Protein Engineering vol. 11, No. 12, pp. 1121-1128, 1998.
Garrote, G, H Dominguez, and JC Parajo, 2001, Manufacture of xylose-based fermentation media from corncobs by posthydrolysis of autohydrolysis liquors, Appl. Biochem. Biotechnol., 95: 195-207.
GenBank: AJ252161.1 Alicyclobacillus acidocaldarius maltose/maltodextrine transport gene region(malEFGR genese, cdaA gene

(56) References Cited

OTHER PUBLICATIONS and glcA gene), NCBI, Hulsmann, A. http://www.ncbi.nlm.nih.gov/nuccore/AJ252161 (Jan. 6, 2000).

GenBank: E17054.1 Direct Submission Alicyclobacillus acidocaldarius genomic DNA clone pOP3 containing acyl carrier protein gene. Nov. 5, 2005 [Retrieved from the Internet Jan. 23, 2010: http://www.ncbi.nlm.nih.gov/nuccore/E17054.1ordinalpos=2 tool=EntrezSystem2. PEntrez.Sequence. Sequence_ ResultsPanel. Sequence_ RVDocSum], 3 pages.

Gessesse, Amare, "Purification and Properties of Two Thermostable Alkaline Xylanases from an Alkaliphilic *Bacillus* sp.," Applied and Environmental Microbiology, Sep. 1998, pp. 3533-3535.

Glenn et al.. Transformation of Acidiphilium by electroporation and conjugation, Can J Microbial. May 1992;38 (5):387-93.

Goldstein et al., The Hydrolysis of Cellulose with Superconcentrated Hydrochloric Acid, Biotechnology and Bioengineering Symp. No. 13, pp. 17-25 (1983).

Grassin et al., "Chapter 2.13, Fruit Juices," (T. Godfrey and S. West, eds.), Industrial Enzymology, 2nd Ed., pp. 227-264 (1996).

Grethlein, H. E., "Pretreatment for enhanced hydrolysis of cellulosic biomass," Biotechnol. Adv. 1984. 2:43-62.

Grethlein, Hans E., "Comparison of the Economics of Acid and Enzymatic Hydrolysis of Newsprint," Biotechnology and Bioengineering, vol. XX, pp. 503-525 (1978).

Guateli, J. C. et al., 1990, PNAS. USA, 87: 1874-1878.

Hamelinck, CN, G van Hooijdonk, and APC Faaij, 2005, Ethanol from lignocellulosic biomass: techno-economic performance in short-, middle-, and long-term, Biomass Bioenergy, 28:384-410.

Hanselmann, KW., "Lignochemicals," Experientia 38 (1982) pp. 176-189.

Houghton et al., "Fungal Upgrading of Wheat Straw for Straw-Thermoplastics Production," Applied Biochemistry and Biotechnology, vol. 113-116, 2004, pp. 71-93.

Hulsmann et al., "Maltose and maltodextrin transport in the thermoacidophilic gram-positive bacterium *Alicyclobacillus acidocaldarius* is mediated by a high-affinity transport system that includes a maltose binding protein tolerantto low pH," J. Bacteriol. 2000, 182(22):6292-6301.

Huygen, K. et al., 1996, Nature Medicine, 2(8): 893-898.

Turner et al., "Potential and utilization of thermophiles and thermostable enzymes in biorefining," Microbial Cell Factories, Biomed Central, London, NL, vol. 6, No. 1, Mar. 15, 2007, p. 9.

Uchikoba et al., "Crystal Structure of Non-Allosteric L-Lactate Dehydrogenase From Lactobacillus pentosus at 2.3 A Resolution: Specific Interactions at Subunit Interfaces," Proteins: Structure, Function, and Genetics, 46:206-214 (2002).

Uhl et al., "The first description of an archaeal hemicellulase: the xylanase from Thermococcus zilligii strain AN 1," Extremophiles (1999) 3:263-267.

Uniprot Direct submission Q9RHZ5_ALIAC, "Putative maltose transport membrane protein malF," Nov. 13, 2007. [Retrieved from the Internet Jan. 22, 2010: http://www.uniprol.org/uniprot/Q9RHZ5.lxtversion=30.

UniProtKB/TrEMBL Q9JRQ1 [online]. Oct. 1, 2000. Available on the internet at URL://http://www.uniprot.org/uniprot/Q9JRQ1.

Upreti et al., 2003, Bacterial glycoproteins: Functions, biosynthesis and applications. Proteomics, 3: 363-379.

Urdea, M. S., 1988, Nucleic Acids Research, II: 4937-4957.

Vieille and Zeikus, 2001, Micro. and Mol. Biol. Rev., vol. 65, No. 1, p. 1-43.

Viikari et al., "Xylanases in bleaching: From an idea to the industry," FEMS Microbiology Reviews 13 (1994) 335-350.

Walker, G. T. et al., 1992, NAR 20: 1691-1696.

Walker, G. T. et al., 1992, PNAS. USA, 89:392-396.

Walseth, Curtis S., Occurrence of Cellulases in Enzyme Preparations from Microorganisms, TAPPI vol. 35, No. 5, May 1952, pp. 228-233.

Ward et al., "Characterization of a new bacteriophage which infects bacteria of the genus *Acidiphilium*," Journal of General Virology (1993) 74: 2419-2425.

Ward et al., "Electrotransformation of Acidophilic, Heterotrophic, Gram-negative Bacteria," Electrotransformation of Bacteria, Natalie Eynard, Justin Teissie (eds.), Springer (2000) pp. 94-103.

Whisstock et al. "Prediction of Protein Function from Protein Sequence and Structure" Quarlty Reviews of Biophysics 36, 3 (2003) pp. 307-340 (35 pages).

Witkowski et al. "Conversion of a r-Ketoacyl Synthase to a Malonyl Decarboxylase by Replacement of the Active-Site Cysteine with Glutamine" American Chemical Society, Biochemistry, vol. 38, No. 36, 1999 pp. 11643-11650 (8 pages).

Wright et al., "Ethanol from Biomass by Enzymatic Hydrolysis," Chemical Engineering Progress, Aug. 1988, pp. 62-74.

Yuan et al., Expression of acidophilic alpha-amylase from Alicyclobacillus acidocaldarius, Sheng Wu Gong Cheng Xue Bao, Jan. 2005, 21(1):78-83. Abstract only.

\* cited by examiner

FIG. 1A

```
15642830     1                        MDYRMCWLEYRGLP.ADVAGKLK
148270004    1                        MDYRMCWLEYRGLP.ADVAKKLK
15613624     1            MNR........GETGYETWLRYEEITDSALHTQYR
118725970    1            MYKSNVNDELYGANGYNCWLGYHLLENGELRENYS
RAAC02661    1              MTNIPEGDLDYRAWLQESPLPRAVPEAARR
116621784    1 MSFKFLALLLTIPAVHAETGYDAWLRYAPLSDAAARPYLT 15642830    23 DWFSSVSILEPGS..SVLKDEIRRFSERSIGITPRFYSRP
148270004   23 DWFSSVSILEPGS..SVLKDEIRRFSERSIGITPGFYSRP
15613624    28 AYFQTIEIKGNSPIIESAKEELMQGLRSLLGVTPKCLSAT
118725970   36 QWASNIVISKEPDEIKIALSELKSGINGILGVDAVVVTRE
RAAC02661   31 ...MAVYGPADDPLLCTAAAEWGRAVRAACGESPARLARD
116621784   41 ALPAAVTVYGASPVVQSAQRELLRGVRGMLGRTLRMESKL 15642830    61 LKKE...KYIMVGRLESLP......IKLD..VNLGEEGFM
148270004   61 LKKE...KYIMVGRLESLP......IKFD..ENLGEEGFM
15613624    68 GEQA...SCL.IGTIADVAE.VSQAIK....ERLREEGYA
118725970   76 PEQS...SCIALGVLGRGQN.IDSYVKYDEVVQIGNEGFI
RAAC02661   68 PGGAPSVPCVAMGLLSAMPRGLREAAQAALAGAPSDEAYA
116621784   81 PAER....AILLGTAGDLQA...AIPQLHLPPDLPADSYL 15642830    90 LRTIEWNGSKILLVTGETKKALVYGIFDLMKRIRLGEDIE
148270004   90 LRTLEWNGSKILLVTGETKKALVYGIFDLMKIIRLGEDIE
15613624    99 IYSEKGR....LVLVGKTETGVLYGTFHLLRLLQMRDHLH
118725970  112 IKAFKTGNSEIVVVAGTTTKGLLYGVFSLLRLLQTEATIS
RAAC02661  108 ILPVDGQG...VAVVSRTPAGVLYGVFHLIRRLRLGEPLH
116621784  114 VTTVTANGAPHLVIAGANDRAVLYGVFALLRKIGTGQTLN 15642830   130 KMNVLAKPKAKFRMLNHWDNLDGTIERGYAGNSIFFKDNR
148270004  130 KMNVLEKPKAKFRMLNHCDNLDGTIERGYAGNSIFFKDNR
15613624   135 DLRIVENPRNQLRMINEWDNMDGSIERGYAGGSIFFEHNK
118725970  152 GILKIENPANQLRIINHWDNIDGSIERGYAGKSIFFTDNK
RAAC02661  145 EP.CVSSPKNAWRMLDHWDNADGTIERGYAGKSLFYRGGQ
116621784  154 DDDPVQTPYAPVRWVNEWNNLDGTIERGYGGRSIFWDNNR 15642830   170 IIIN.QRTKDYARLLASIGINGVVINNVNVKKREVYLIDS
148270004  170 IIIN.QRTKDYARLLASIGINGVVINNVNVKKREVYLIDS
15613624   175 VTNNLQRIKDYARILSSIGINAIAFNNVNVHEEETKLITR
118725970  192 VTEDLGRIKDYARLLCSVGINSIVINNVNVHKYESMLITD
RAAC02661  184 IDFDEGRVRDYARLLASVGVNAIAINNVNVHETETRFLTE
116621784  194 ARADLTRVADYGRMLASLGIQACSINNVNAN...PRVLAS 15642830   209 IYLKKLKKLADIFREYGIKIYLSINFASPVYLGGLDTADP
148270004  209 IYLKRLKKLADIFREYGIKIYLSINFASPVYLRGLDTADP
15613624   215 KFLPDVAKVANIFRQYGIKTFLSINYASPIQLGKLETADP
118725970  232 KYLNDVASLAQIFRDYGIKLYLSANFASTIEIGGLATADP
RAAC02661  224 AHLPGVARLADVFRPYGIRVFLSINFASPVDLGDLPTADP
116621784  231 DFLPEIVRIAEAFRPWGIRVALAVDFGSPKTIGGLDTFDP
```

FIG. 1B

```
15642830    249  LDERVARWWREKARGIYDYIPDFGGFLVKADSEFNPGPHM
148270004   249  LDERVAHWWREKAREIYDHIPDFGGFLVKADSEFNPGPHM
15613624    255  LDEKVRAWWKETVADIYRYIPDFGGFLVKADSEHRPGPFT
118725970   272  LDPQVRKWWKEKADEIYSLIPDFGGFLIKADSEFRPGPFT
RAAC02661   264  LDPRVEDWWRATADRIYRHIPDFGGFLVKADSEFRPGPFT
116621784   271  VDPKVAAWWKSKIDELYRAVPDLAGIVLKADSEGRVGPST 15642830    289  FGRTHAEGANMLARALAPFGGVVIWRAFVYNCLQDWRDYK
148270004   289  FGRTHAEGANMLARALAPFGGVVIWRAFVYNCLQDWRDYK
15613624    295  YGRNHAEGANMLAEALAPFGGIVLWRCFVYNCLQDWRDRK
118725970   312  YGRTHADGANMLAEALEPYGGLVIWRCFVYNCMQDWRDRI
RAAC02661   304  YGRDHADGANMLARALAPHGGVVIWRAFVYNCLMDWRDRR
116621784   311  YGRTHADAANVVARGLQPHGGLLFYRGFVYDHHMDWKNPK 15642830    329  TDRAKAAYDNFKPLDGQFDDNVIIQIKYGPMDFQVREPVN
148270004   329  TDRAKAAYDNFKPLDGQFDDNVIIQIKYGPMDFQVREPVN
15613624    335  TDRARAAYDHFKPLDGLFHDNVVLQIKNGPMDFQVREPVS
118725970   352  TDRARAAYDNFMPLDGLFRENVLLQIKNGPMDFQVREPVS
RAAC02661   344  ADRARAAYDHFVPLDGRFLDNVLIQIKNGPMDFQVREPVS
116621784   351  NDRGRAAYDNFQPLDGKFDANVIVQIKHGPIDFQVREPAS 15642830    369  PLFGGMEKTNQILELQITQEYTGQQIHLCFLGTLWKEILE
148270004   369  PLFGGMERTNQILELQITQEYTGQQIHLCFLGNLWKEILE
15613624    375  PLFGAMPKTNQMLEFQITQEYTGQQKHLCYLVPQWKEILD
118725970   392  PLFGGLQKTNQLLELQITQEYTGQQKHLCYLVPMWKEILD
RAAC02661   384  PLFGGLSATNVMLEFQITQEYTGQQRHVCYLAPMWKEVLD
116621784   391  PLFAALEKTNQAIELQITQEYFGQSRHNVFLVPMWKTALD 15642830    409  FDTFAKGEGSYVKRIVDGTLFDRENNGFAGVSNVGDSVNW
148270004   409  FDTFAKGEGSYVKRIVDGTLFDRKNNGFAGVSNVGDSVNW
15613624    415  FDTFANGKESPVKSIVDGSQYDYKVSGITAVSNVGNDENW
118725970   432  FDTMAKGRNTSVKKIITGSVFNNKLGGMAAVTNIGNDLNW
RAAC02661   424  FDTHARGPGSTVAEIASGRLFGRPHGGVAGVANVGDDVNW
116621784   431  FDMQAGG.TTPVKALAAGKVFHRPIGGFVGVSNIGLDDNW 15642830    449  TGHDLAQANLYAFGRLAWNPDEEIERIVEEWIKLTFGDDE
148270004   449  TGHDLAQANLYAFGRLAWNPDEEIERIVEEWIKLTFGDDE
15613624    455  TGHLLAQANLYGYGRLTWNPNLSTEEVTTEWTRATFGDNE
118725970   472  TGHQMAQSNTYGYARLCWNPDLSAEKITDEWVRMTYSNYE
RAAC02661   464  TGHSLAQANLYAFGRLAWDPSLDPAGIAREWARLTYGDDP
116621784   470  SGNQLSQANLYGFGRLAWNPDLTSQQIIDEWTRLTFGNEP 15642830    489  KVLENVSYMLMKSHRTYEKYTTPFGLWMVN.PGHHYGPN
148270004   489  KVLENVSYMLMKSHRTYEKYTTPFGLWMVN.PGHHYGPN
15613624    495  EVIQTIHEMLLQSWLIYESYTAPLGVWMVE.PGHHYGPN
118725970   512  KVVNTVKEMLLGSWRTYENYTSPLGIGWMVN.PNHHYGPN
RAAC02661   504  DVVRTVVGILMASWPAYEAYTAPLGVWMVN.PGHHDGPN
116621784   510  KTVETITAMQLASWPVFEKYTGPLGLQTLTDIVGDHYGVA
```

FIG. 1C

```
15642830    528  PEGYEYSKWGTYHRANWEAIGVDRTSR.GTGYTLQYHSPW
148270004   528  PEGYEYSKWGTYHRANWEAIGVDRTSR.GTGYTLQYHSPW
15613624    534  VDGYEYSVWGTYHYADCHGIGVDRTVATGTGYTAQYFAEN
118725970   551  VDGYEYDKWGTYHRADHKGIGVDRTVKSGTGYAGQYHKDV
RAAC02661   543  PEGYEYSKWGTYHYADWRGVGVDRTMATGTGYTGQYHEPM
116621784   550  VEASEHNGWGQWHNADEKGVGMDRTVATGTGYIGQYRPPV 15642830    567  KEIYDDINTCPEDLLLFFHRVRYDHRLKSGKTLLQTMYDL
148270004   567  KEIYDDINTCPEDLLLFFHRVRYDHRLKSGKTLLQTIYDL
15613624    574  YELYEHLETCPDSLLLFFHHVPYTHKLKSGVTVIQHIYDT
118725970   591  AGIYEDMDKCPEELLLFFHHMPYDYILKSGETLIQYIYNT
RAAC02661   583  RSLYEHLETCPDELLLFFHHVPYTHVLHSGKTVIQHIYDA
116621784   590  AKMYESLETCPDDLLLFLHHVPYTYKLHSGKTVIQYLYDS 15642830    607  HFEGVEEVEEFIKKWEELKDRVSPDIFERVKERLHMQLEH
148270004   607  HFEGVEEVEEFIKKWEELKDRVPPDIFERVKERLHMQLEH
15613624    614  HFSGAEQAEQLLESWRSLEGKVDSERFQQVLERLEHQAEH
118725970   631  HFKGVEEVEELRNKWFSLKGWISEEIFLHVLERLDGQLEH
RAAC02661   623  HFDGVEAVAWMIEAWRRLQGRIDPVRFERVLARLEDQMQR
116621784   630  HYEGADAVAAWVRDFQSLRGHIDDQRYNEVLAQLRYQAAH 15642830    647  AKEWRDVINTYFYRRTGIPDEKGRK...............
148270004   647  AKEWRDVINTYFYRRTGIPDEKGRK...............
15613624    654  AKEWRDVINTYFYRKSGIPDEKKRT...............
118725970   671  SKEWRDVINTYFYRKTGISDELGRK...............
RAAC02661   663  AVEWRDVINTYFYRKCGIPDARGLH...............
116621784   670  VEVWRDAVNNWFHRESGIADAKGRVGNHPGRSEAEAMKLE 15642830    672  ......IYP
148270004   672  ......IYP
15613624    679  ......IYPI
118725970   696  ......IY
RAAC02661   688  ......IYP
116621784   710  GYTVAEITPWESASGGKAVTCPASKCTASMQFSGAPGWYT 15642830
148270004
15613624
118725970
RAAC02661
116621784   750  LRVQYFDLNGPVSSFKLWVGNQLVDEWSATDHLPARKLDA 15642830
148270004
15613624
118725970
RAAC02661
116621784   790  SSSTRREVSGIALRPGDQVRIEAIPEGRELAALDYLEILP
```

FIG. 1D

```
15642830
148270004
15613624
118725970
RAAC02661
116621784    830 NEPRQ
```

METHODS OF COMBINED BIOPROCESSING AND RELATED MICROORGANISMS, THERMOPHILIC AND/OR ACIDOPHILIC ENZYMES, AND NUCLEIC ACIDS ENCODING SAID ENZYMES

CROSS-REFERENCE TO RELATED APPLICATIONS

This application is a continuation of U.S. patent application Ser. No. 15/676,484, filed Aug. 14, 2017, pending, which is a continuation of U.S. patent application Ser. No. 15/074,297, filed Mar. 18, 2016, now U.S. Pat. No. 9,732,330, which is a continuation-in-part of U.S. patent application Ser. No. 14/185,501, filed Feb. 20, 2014, now U.S. Pat. No. 9,290,784, issued Mar. 22, 2016, which is a continuation-in-part of U.S. patent application Ser. No. 13/924,149, filed Jun. 21, 2013, now U.S. Pat. No. 8,691,525, issued Apr. 14, 2014, which is a divisional of U.S. patent application Ser. No. 12/587,229, filed Oct. 2, 2009, now U.S. Pat. No. 8,492,114, issued Jul. 23, 2013, which is a continuation-in-part of U.S. patent application Ser. No. 12/322,359, filed Jan. 29, 2009, now U.S. Pat. No. 7,858,353, issued Dec. 28, 2010, to Thompson et al., which claims the benefit of U.S. Provisional Patent Application Ser. No. 61/025,136, filed Jan. 31, 2008, for "THERMOPHILIC AND THERMOACIDOPHILIC BIOPOLYMER-DEGRADING GENES AND ENZYMES FROM *ALICYCLOBACILLUS ACIDOCALDARIUS* AND RELATED ORGANISMS, METHODS"; and U.S. patent application Ser. No. 12/587,229 is a continuation-in-part of U.S. patent application Ser. No. 12/380,551, filed Feb. 26, 2009, now U.S. Pat. No. 8,728,803, issued May 20, 2014, to Thompson et al., which claims the benefit of U.S. Provisional Patent Application Ser. No. 61/032,339, filed Feb. 28, 2008, for "THERMOPHILIC AND THERMOACIDOPHILIC METABOLISM GENES AND ENZYMES FROM *ALICYCLOBACILLUS ACIDOCALDARIUS* AND RELATED ORGANISMS, METHODS"; and U.S. patent application Ser. No. 12/587,229 is a continuation-in-part of U.S. patent application Ser. No. 12/380,450, filed Feb. 26, 2009, now U.S. Pat. No. 9,234,228, issued Jan. 12, 2016, to Thompson et al., which claims the benefit of U.S. Provisional Patent Application Ser. No. 61/031,984, filed Feb. 27, 2008, for "THERMOPHILIC AND THERMOACIDOPHILIC GLYCOSYLATION GENES AND ENZYMES FROM *ALICYCLOBACILLUS ACIDOCALDARIUS* AND RELATED ORGANISMS, METHODS"; and U.S. patent application Ser. No. 12/587,229 is a continuation-in-part of U.S. patent application Ser. No. 12/380,554, filed Feb. 26, 2009, now U.S. Pat. No. 7,960,534, issued Jun. 14, 2011, to Thompson et al., which claims the benefit of U.S. Provisional Patent Application Ser. No. 61/031,593, filed Feb. 26, 2008, for "THERMOPHILIC AND THERMOACIDOPHILIC SUGAR TRANSPORTING GENES AND ENZYMES FROM *ALICYCLOBACILLUS ACIDOCALDARIUS* AND RELATED ORGANISMS, METHODS"; and U.S. patent application Ser. No. 12/587,229 is a continuation-in-part of U.S. patent application Ser. No. 12/380,008, filed Feb. 20, 2009, now U.S. Pat. No. 8,716,011, issued May 6, 2014, to Lee et al., which claims the benefit of U.S. Provisional Patent Application Ser. No. 61/030,820, filed Feb. 22, 2008, for "TRANSCRIPTIONAL CONTROL IN *ALICYCLOBACILLUS ACIDOCALDARIUS* AND ASSOCIATED GENES, PROTEINS, AND METHODS"; and U.S. patent application Ser. No. 12/587,229 is a continuation-in-part of U.S. patent application Ser. No. 12/321,636, filed Jan. 23, 2009, now U.S. Pat. No. 7,923,234, issued Apr. 12, 2011, to Thompson et al., which claims the benefit of U.S. Provisional Patent Application Ser. No. 61/023,639, filed Jan. 25, 2008, for "THERMAL AND ACID TOLERANT BETA-XYLOSIDASES, GENES ENCODING, RELATED ORGANISMS, AND METHODS"; the disclosure of each of which is hereby incorporated herein in its entirety by this reference.

This application is related to U.S. patent application Ser. No. 14/887,073, filed Oct. 19, 2015, pending, which is a divisional of U.S. patent application Ser. No. 14/226,573, filed Mar. 26, 2014, now U.S. Pat. No. 9,222,094, issued Dec. 29, 2015, which is a divisional of U.S. patent application Ser. No. 12/380,551, filed Feb. 26, 2009, now U.S. Pat. No. 8,728,803, issued May 20, 2014, to Thompson et al. which claims the benefit of U.S. Provisional Patent Application Ser. No. 61/025,136, filed Jan. 31, 2008. This application is also related to U.S. patent application Ser. No. 14/977,349, filed Dec. 21, 2015, pending, which is a divisional of U.S. patent application Ser. No. 12/380,450, filed Feb. 26, 2009, now U.S. Pat. No. 9,234,228, issued Jan. 12, 2016, to Thompson et al., which claims the benefit of U.S. Provisional Patent Application Ser. No. 61/031,984, filed Feb. 27, 2008. This application is also related to U.S. patent application Ser. No. 13/721,172, filed Dec. 20, 2012, now U.S. Pat. No. 8,575,323, issued Nov. 5, 2013, which is a divisional of U.S. patent application Ser. No. 13/517,887, filed Jun. 14, 2012, now U.S. Pat. No. 8,362,226, issued Jan. 29, 2013, which is a divisional of U.S. patent application Ser. No. 13/200,164, filed Sep. 20, 2011, now U.S. Pat. No. 8,354,517, issued Jan. 15, 2013 which is a divisional of U.S. patent application Ser. No. 13/066,645, filed Apr. 19, 2011, now U.S. Pat. No. 8,071,748, issued Dec. 6, 2011, which is a divisional of U.S. patent application Ser. No. 12/380,554, filed Feb. 26, 2009, now U.S. Pat. No. 7,960,534, issued Jun. 14, 2011, to Thompson et al., which claims the benefit of U.S. Provisional Patent Application Ser. No. 61/031,593, filed Feb. 26, 2008. This application is also related to U.S. patent application Ser. No. 14/920,598, filed Oct. 22, 2015, now U.S. Pat. No. 9,499,824, issued Nov. 22, 2016, which is a divisional of U.S. patent application Ser. No. 14/256,819, filed Apr. 18, 2014, now U.S. Pat. No. 9,187,753, issued Nov. 17, 2015 which is a divisional of U.S. patent application Ser. No. 12/380,008, filed Feb. 20, 2009, now U.S. Pat. No. 8,716,011, issued May 6, 2014, to Lee et al., which claims the benefit of U.S. Provisional Patent Application Ser. No. 61/030,820, filed Feb. 22, 2008, the disclosure of each of which is hereby incorporated herein in its entirety by this reference.

GOVERNMENT RIGHTS

This invention was made with government support under Contract Number DE-AC07-99ID13727 and Contract Number DE-AC07-05ID14517 awarded by the United States Department of Energy. The government has certain rights in the invention.

STATEMENT ACCORDING TO 37 C.F.R. § 1.821(c) or (e)—SEQUENCE LISTING SUBMITTED AS A TXT

Pursuant to 37 C.F.R. § 1.821(c) or (e), files containing a TXT version of the Sequence Listing have been submitted concomitant with this application, the contents of which are hereby incorporated by reference.

BACKGROUND

Dilute acid hydrolysis to remove hemicellulose from lignocellulosic materials is one of the most developed pretreatment techniques for lignocellulose and is currently favored (Hamelinck et al., 2005) because it results in fairly high yields of xylose (75% to 90%). Conditions that are typically used range from 0.1 to 1.5% sulfuric acid and temperatures above 160° C. The high temperatures used result in significant levels of thermal decomposition products that inhibit subsequent microbial fermentations (Lavarack et al., 2002). High temperature hydrolysis requires pressurized systems, steam generation, and corrosion resistant materials in reactor construction due to the more corrosive nature of acid at elevated temperatures.

Lower temperature acid hydrolyses are of interest because they have the potential to overcome several of the above shortcomings (Tsao et al., 1987). It has been demonstrated that 90% of hemicellulose can be solubilized as oligomers in a few hours of acid treatment in the temperature range of 80° C. to 100° C. It has also been demonstrated that the sugars produced in low temperature acid hydrolysis are stable under those same conditions for at least 24 hours with no detectable degradation to furfural decomposition products. Finally, sulfuric acid typically used in pretreatments is not as corrosive at lower temperatures. The use of lower temperature acid pretreatments requires much longer reaction times to achieve acceptable levels of hydrolysis. Although 90% hemicellulose solubilization has been shown (Tsao, 1987), the bulk of the sugars are in the form of oligomers and are not in the monomeric form. The organisms currently favored in subsequent fermentation steps cannot utilize sugar oligomers (Garrote et al., 2001) and the oligomer-containing hydrolysates require further processing to monomers, usually as a second acid or alkaline hydrolysis step (Garrote et al., 2001).

Other acidic pretreatment methods include autohydrolysis and hot water washing. In autohydrolysis, biomass is treated with steam at high temperatures (~240° C.), which cleaves acetyl side chains associated with hemicellulose to produce acetic acid that functions in a similar manner to sulfuric acid in acid hydrolysis. Higher pretreatment temperatures are required as compared to dilute sulfuric acid hydrolysis because acetic acid is a much weaker acid than sulfuric. At temperatures below 240° C., the hemicellulose is not completely hydrolyzed to sugar monomers and has high levels of oligomers (Garrote et al., 2001). In hot water washing, biomass is contacted with water (under pressure) at elevated temperatures 160° C. to 220° C. This process can effectively hydrolyze greater than 90% of the hemicellulose present, and the solubilized hemicellulose was typically over 95% in the form of oligomers (Liu and Wyman, 2003).

BRIEF SUMMARY

The entire contents of each of the following applications and patents are incorporated herein in their entirety by this reference: patent application Ser. No. 12/322,359, filed Jan. 29, 2009, now U.S. Pat. No. 7,858,353, issued Dec. 28, 2010, to Thompson et al.; Ser. No. 12/321,636, filed Jan. 23, 2009, now U.S. Pat. No. 7,923,234, issued Apr. 12, 2011, to Thompson et al.; Ser. No. 12/380,008 filed Feb. 20, 2009, now U.S. Pat. No. 8,716,011, issued May 6, 2014, to Lee et al.; Ser. No. 12/380,554, filed Feb. 26, 2009, now U.S. Pat. No. 7,960,534, issued Jun. 14, 2011, to Thompson et al.; Ser. No. 12/380,450 (filed Feb. 26, 2009); and Ser. No. 12/380,551 filed Feb. 26, 2009, now U.S. Pat. No. 8,728,803, issued May 20, 2014, to Thompson et al.

Embodiments of the invention relate to a genetically modified organism for converting biomass into products. The genetically modified organism may comprise at least one nucleic acid sequence encoding a polypeptide as disclosed in the patent applications and patents previously incorporated by reference herein. In embodiments, the genetically modified organism may comprise at least one nucleic acid sequence encoding a polypeptide associated with at least partially degrading, cleaving, transporting, metabolizing and/or removing polysaccharides, cellulose, hemicellulose, lignin, starch, sugars, sugar oligomers, carbohydrates, complex carbohydrates, chitin, heteroxylans, glycosides, xylan-, glucan-, galactan-, or mannan-decorating groups; and/or at least one nucleic acid sequence encoding a polypeptide associated with fermenting sugar molecules to products.

Embodiments of the invention also relate to protein(s) and/or cellular extracts isolated from a genetically modified organism. The isolated protein and/or cellular extracts may comprise: at least one polypeptide isolated from a genetically modified organism, the organism including: at least one recombinant nucleic acid encoding a polypeptide as disclosed in the patent applications and patents previously incorporated by reference herein. In embodiments, the at least one recombinant nucleic acid encoding a polypeptide may comprise: at least one polypeptide involved in at least partially degrading, cleaving, transporting, metabolizing and/or removing polysaccharides, cellulose, hemicellulose, lignin, starch, sugars, sugar oligomers, carbohydrates, complex carbohydrates, chitin, heteroxylans, glycosides, xylan-, glucan-, galactan-, or mannan-decorating groups; and/or at least one recombinant nucleic acid encoding a polypeptide involved in fermenting sugar molecules to products.

Additional embodiments of the invention relate to methods of at least partially processing polysaccharides, cellulose, hemicellulose, starch, sugars, sugar oligomers, carbohydrates, complex carbohydrates, chitin, heteroxylans, glycosides, xylan-, glucan-, galactan-, or mannan-decorating groups into a product. The method may comprise: placing a genetically modified organism in fluid contact with a polysaccharide, cellulose, hemicellulose, starch, sugars, sugar oligomers, carbohydrates, complex carbohydrates, chitin, heteroxylans, glycoside, xylan-, glucan-, galactan-, and/or mannan-decorating group. The genetically modified organism may comprise at least one nucleic acid and/or at least one recombinant nucleic acid encoding a polypeptide involved in at least partially degrading, cleaving, transporting, metabolizing, or removing polysaccharides, cellulose, hemicellulose, lignin, starch, sugars, sugar oligomers, carbohydrates, complex carbohydrates, chitin, heteroxylans, glycosides, xylan-, glucan-, galactan-, or mannan-decorating groups; and/or at least one nucleic acid and/or at least one recombinant nucleic acid encoding a functional protein involved in fermenting sugar molecules to a product and/or a fermentation enzyme involved in converting sugars into a product.

Further embodiments of the invention relate to isolating an extract from a genetically modified organism according to the present invention. Embodiments may also include placing the isolated extract in fluid contact with a polysaccharide, cellulose, hemicellulose, lignin, starch, sugars, sugar oligomers, carbohydrates, complex carbohydrates, chitin, heteroxylans, glycoside, xylan-, glucan-, galactan-, and/or mannan-decorating group. The genetically modified organism may comprise at least one nucleic acid and/or at least one recombinant nucleic acid encoding a polypeptide having some level of activity in at least partially degrading, cleaving, transporting, metabolizing, and/or removing polysaccharides, cellulose, hemicellulose, lignin, starch, sugars, sugar oligomers, carbohydrates, complex carbohydrates, chitin, heteroxylans, glycosides, xylan-, glucan-, galactan-, or mannan-decorating groups; and/or at least one nucleic acid and/or at least one recombinant nucleic acid encoding a functional protein involved in fermenting sugar molecules to a product such as a fermentation or other enzyme involved in converting sugars into a product.

BRIEF DESCRIPTION OF THE DRAWINGS

FIGS. 1A-ID depict a sequence alignment between SEQ ID NO:337 (RAAC02661), a xylan alpha-1,2-glucuronidase, and gi|15613624, gi|118725970, gi|148270004, gi|5642830, and gi|16621784 (SEQ ID NOs:338-342, respectively) which are all xylan alpha-1,2-glucuronidases. Amino acids common to three or more of the sequences aligned are indicated in bold.

DETAILED DESCRIPTION

Figure 2:
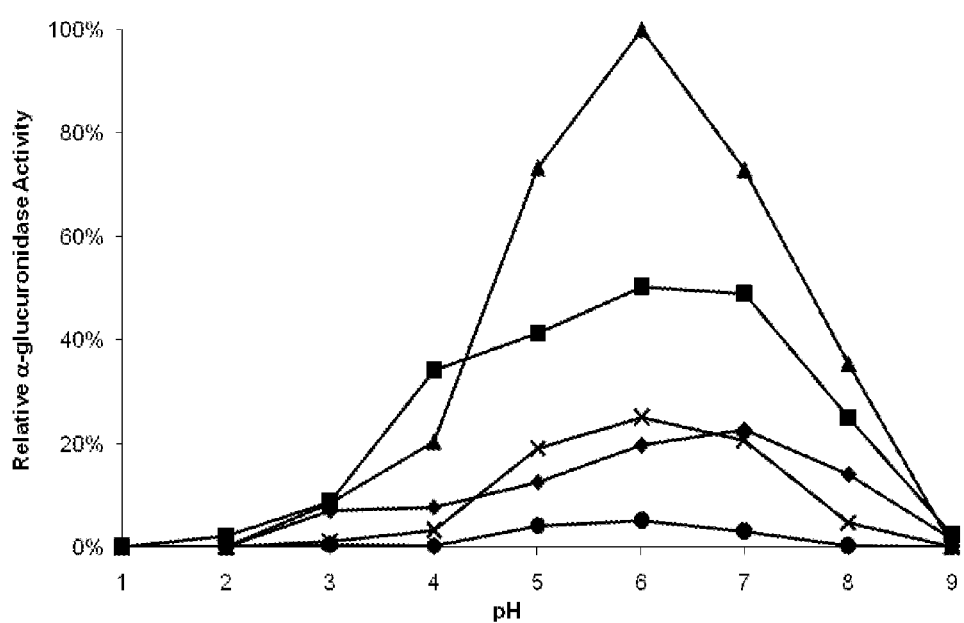
FIG. 2 is a graphical representation of the relative α-glucuronidase (AGUR) activity of RAAC02661 (SEQ ID NO:337) produced in *E. coli*. Diamonds indicate the activity at 50° C., squares indicate the activity at 60° C., triangles indicate the activity at 70° C., Xs indicate the activity at 80° C., and circles indicate the activity at 90° C.

Lignocellulose is a highly heterogeneous three-dimensional matrix comprised of cellulose, hemicellulose, and lignin. Many fuels and chemicals can be made from these lignocellulosic materials. To utilize lignocellulosic biomass for production of fuels and chemicals via fermentative processes, it is necessary to convert the plant polysaccharides to simpler sugars, which are then fermented to products using a variety of organisms. Direct hydrolysis of cellulose by mineral acids to monomers is possible at high temperature and pressure, leading to yield losses due to thermal decomposition of the sugars. One strategy to reduce these yield losses is to use cellulases and potentially other enzymes to depolymerize the polysaccharides at moderate temperatures. Addition of acid-stable thermotolerant hydrolytic enzymes such as cellulases and xylanases to the biomass slurry during the pretreatment allows the use of lower temperatures and pressures, as well as cheaper materials of reactor construction, reducing both the capital and energy costs. Another approach is to combine the reduced severity pretreatment with enzymes together with fermentation under the same conditions, using a single organism that produces the enzymes to degrade the material as well as ferment the sugars to the value-added product of choice.

For commercially available enzymes to be used for this purpose, the pretreatment slurry must be neutralized and cooled to 40° C. to 50° C., adding significant cost to the process. Hence, it would be an improvement in the art to degrade the soluble oligomers produced using acid, autohydrolysis or hot water washing pretreatments, at reduced severity and without neutralization using, for example, thermophilic and/or acidophilic enzymes.

Embodiments of the invention relate to a genetically modified organism comprising at least one of a nucleic acid sequence and protein sequence encoded by a nucleic acid sequence from *Alicyclobacillus acidocaldarius*. Such nucleic acids may include any of those nucleotide sequences described in the patent applications and patents incorporated herein by reference. Such nucleic acids include, but are not limited to, those coding for enzymes capable of depolymerizing cellulosic polysaccharides to simpler carbohydrates and their transport into the bacterial cell and metabolism within the cell. Enzyme activities associated with transport into the cell and metabolism within the cell may be thermophilic and/or acidophilic in nature and general examples of nucleic acids coding for similar enzymes are described in the literature. Enzyme activities associated with cellulose depolymerization and/or metabolism may be thermophilic (intracellular) and/or thermoacidophilic (extracellular) and include, without limitation, the following classes of enzymes: Alpha-glucosidases, Glucan 1,4-alpha-maltohydrolases, Glycosidases, Amylases, Acetyl esterases, Beta-galactosidases, Alpha amylases, Alpha-xylosidases, Cyclomaltodextrinases; Neopullulanases; Maltogenic alpha-amylases, Family 31 of glycosyl hydrolase, Alpha-L-arabinofuranosidases, Altronate hydrolases, poly-1,4-alpha-D-galacturonidase, Xylan alpha-1,2-glucuronosidases, Cellulase/Endoglucanase, Polygalacturonases, Glycosyl hydrolases, Peptidoglycan hydrolases, N-acetylglucosaminidases, Endochitinases, Alpha-galactosidases, Endo-beta-1,4-mannanases, Cellobiose phosphorylases, Cyclic beta-1,2-glucan synthases, Glycogen debranching enzymes, Acetyl hydrolases, Beta-1,4-xylanases, Beta-glucosidases, 6-phospho-beta-glucosidases, Cinnamoyl ester hydrolases, Beta-glucuronidases, Xylan alpha-1,2-glucuronosidases, 3-hydroxyisobutyryl-CoA hydrolases, glycosidases, Chitooligosaccharide deacetylases, glycosyl hydrolases (or glycoside hydrolases); esterases including acetylxylan esterases and p-cumaric acid esterases and ferulic acid esterases; and/or uronidases.

Additionally, embodiments of the invention relate in part to a genetically modified organism comprising, in addition to at least one of the nucleic acid sequences and protein sequences encoded by nucleic acids of *Alicyclobacillus acidocaldarius*, at least one of the nucleic acid sequences and protein sequences associated with fermenting sugar molecules to products. Such nucleic acid sequences may code for protein sequences which may be thermophilic and/or acidophilic in nature and general examples of similar nucleic acids are described in the literature.

The present invention also relates to isolated and/or purified nucleotide sequences from the genome of *Alicyclobacillus acidocaldarius* selected from the sequences described in the patent applications and patents previously incorporated herein by reference.

Nucleotide, polynucleotide, or nucleic acid sequence will be understood according to the present invention as meaning either double-stranded or single-stranded DNA and the transcription products of said DNAs.

As used herein, "fermentation" relates to the biological conversion of a sugar molecule into a product. As used herein, a "product" is any chemical that can be made, at least in part, through a biological process. Examples of products include, but are not limited to, ethanol, acetic acid, glyoxylic acid, oxalic acid, lactic acid, 3-hydroxypropionic acid, glycerol, 1,2-propanediol, 1,3-propanediol, propionic acid, acetone, fumaric acid, succinic acid, malic acid, butyric acid, 1-butanol, 2,3-butanediol, acetoin, aspartic acid, 1,2,-butanediol, itaconic acid, glutamic acid, citric acid, aconitic acid, cis-cis muconic acid, gluconic acid, kojic acid, amino acids, vitamins, alginate, cellulose, curdlan, chondroitin, cyanophycin, gellan, heparin, hyaluronic acid, poly-gamma-glutamic acid, poly-epsilon-lysine, polyhydroxyalkanoates, pullulan, scleroglucan, xanthan, indigo, and those chemicals set forth in the BREW report from the University of Utrect, (Patel, M. et al., (2006), "Medium and long-term opportunities and risks of the biotechnological production of bulk chemicals from renewable resources: The potential of white biotechnology." The BREW Project. Final Report prepared under the European Commission's GROWTH Programme (DG Research), (publica.fraunhofer.de/eprints/N-48834.pdf)), the entirety of the contents of which are incorporated herein by this reference.

Although the following sections related to Hydrolysis Associated Molecules (HAMs) and Fermentation Associated Molecules (FAMs), the techniques therein apply equally to all other nucleotide sequences isolated and/or purified from the genome of acidophilic and or thermophilic organisms, such as, without limitation, *Alicyclobacillus acidocaldarius* and those HAMs and FAMs described in the patent applications and patents previously incorporated herein by reference.

Expression/Integration of Hydrolysis Associated Molecules

In embodiments of the invention, one or more Hydrolysis Associated Molecules (HAMs) may be incorporated and/or inserted into an organism that has the ability to ferment sugars to products. The HAMs may include regulatory factors and/or nucleic acids coding for proteins associated with, involved in, and/or assisting in the breakdown and/or hydrolysis of biomass (i.e., polysaccharides, cellulose, lignocellulose, hemicellulose, lignin, starch, sugars, sugar oligomers, carbohydrates, complex carbohydrates, chitin, heteroxylans, glycosides, xylan-, glucan-, galactan-, or mannan-decorating groups, etc.) into more simple sugar molecules and/or sugar monomers. A non-exhaustive list of these proteins and/or enzymes include: cellulases (i.e., endo- and/or exo-cellulases such as endo-beta-1,4-glucanase or exo-beta-1,4-glucanase); hemicellulases (i.e., exo- and/or endo-beta-1,4-xylanase); one or more beta-xylosidase enzymes; β-1,4-cellobiohydrolases (CBH I & CBH II); xylanases (XYN I & XYN II); β-glucosidase; α-L-arabinofuranosidase; acetyl xylan esterase; β-mannanase; and α-glucuronidase; esterases of the alpha-beta hydrolase superfamily; alpha-beta hydrolase; alpha-glucosidases; alpha-xylosidase; alpha-L-arabinofuranosidase; altronate hydrolase; a cellulose/endoglucanase; a polygalacturonase; an alpha-galactosidase; a cellobiose phosphorylase; a glycogen debranching enzyme; an acetyl esterase/acetyl hydrolase; a beta-1,4-xylanase; a cinnamoyl ester hydrolase; a carboxylesterase type B; a beta-galactosidase/beta-glucuronidase; a xylan alpha-1,2-glucuronidase; a 3-hydroxyisobutyryl-CoA hydrolase; a beta-glucosidase B-related glycosidase; and/or a chitooligosaccharide deacetylase and/or so forth. Additional proteins and/or enzymes may include ligninolytic enzymes such as manganese peroxidase, lignin peroxidase, or the like.

Additionally, in embodiments, the HAMs may encompass all those nucleic acids and/or proteins associated with the replication, transcription, translation, and/or expression of nucleic acids involved with the breakdown and/or hydrolysis of biomass and/or lignocellulose into more simple sugar molecules and/or sugar monomers. In a non-limiting example, HAMs may comprise those nucleic acids involved with the regulation of hydrolysis, such as, but not limited to, those nucleic acids and/or proteins that increase the replication, transcription, expression, etc., of HAMs. Further, HAMs may comprise those nucleic acids and/or proteins that are involved with the down-regulation of other HAMs. A non-exhaustive list of these regulatory HAMs may include: transcription factors, enhancers, repressors, DNA binding proteins, or the like.

In embodiments, the HAMs may include derivatives, analogs, and/or modified versions of one or more HAMs. These derivative, analogs, and/or modified versions may include those modifications carried out in vivo or in vitro. Some non-limiting examples of derivative, analogs, and/or modifications include: substitutions, deletions, mutations, modifications etc. Modifications may comprise all modifications occurring to nucleic acids, DNA, RNA, proteins, etc., such as, but not limited to, acetylation, deacetylation, alkylation, methylation, demethylation, carboxylation, glycosylation, phosphorylation, hydroxylation, PEGylation, biotinylation, and/or any other type of modification known in the art.

In embodiments, the HAMs may encompass those nucleic acids, proteins, and/or enzymes that are derivatives of HAMs and include tags, markers, and/or other modifications. A non-exhaustive list of tags may include: His-tags, FLAG tags, Calmodulin-tags, HA-tags, Maltose binding protein-tags, Thioredoxin-tags, S-tags, Strep-tags, Nus-tags, or the like. The HAMs may also include those nucleic acids, proteins, and/or enzymes that include fluorescent markers, such as, but not limited to, GFP, RFP, YFP, BFP, or the like.

In additional embodiments, HAMs may encompass nucleic acid or peptide signals that direct secretion of HAM proteins from the cell in which they are produced. Examples of such signals include N-terminal and/or C-terminal sequences that direct localization and/or secretion of the molecules with which they are associated. In further embodiments, HAMs may include transporter proteins, such as, by way of non-limiting example, ABC transporter proteins that direct the secretion of particular molecules (such as other HAMs) to the extracellular or periplasmic space. In embodiments, the signals may direct secretion of a HAM through any system for secretion including, but not limited to, Endoplasmic Reticulum/Golgi Apparatus systems; vesicle mediated secretion systems; any of the Type I, II, III, IV, V, VI, and/or Tat secretion systems; and/or Sec pathway systems.

The incorporation of the HAMs into the one or more organisms with the ability to ferment sugars to products may enable the one or more organisms to convert cellulosic and/or other biomass compositions into products in a variety of pH and temperature conditions. In one embodiment, the one or more genetically modified organisms may carry out the biomass conversion in a range of pH conditions from at or less than a pH of about 7; at or less than a pH of about 5, about a pH of 1 to about a pH of 5; and/or from about a pH of 1 to about a pH of 1.3.

In embodiments, the ability of a genetically modified organism according to the present invention to function and/or convert biomass into products in pH conditions of 1 to 5, may eliminate the need to neutralize and/or increase the pH to a range of about 5 to 6.0 for enzymatic hydrolysis and/or fermentation after dilute acid pretreatment, which, using conventional methods, is necessary for the hydrolysis and fermentation of cellulose to products. Indeed, in conventional methods of dilute acid hydrolysis, the pretreatment hydrolysate needs to be neutralized to enable enzymatic hydrolysis and fermentation to occur. As such, in one embodiment, the HAMs may code for thermophilic, thermoacidophilic, and/or acidophilic enzymes, properties and/or characteristics, or in the alternative they may be derived from one or more thermophilic, thermoacidophilic, and/or acidophilic organisms.

It is additionally contemplated that one or more of the HAM encoded proteins may function and/or have an optimum pH range of above a pH of 5. Indeed, one or more of the HAMs may function and/or enable breakdown and/or hydrolysis of biomass and/or cellulose into more simple sugar molecules and/or sugar monomers in pH conditions that range from a pH of about 5 to a pH of about 14.

In embodiments, one or more HAMs may function to and/or assist in the breakdown and/or hydrolysis of biomass and/or cellulosic materials into more simple sugar molecules and/or sugar monomers in a broad range of temperatures. Conventional methods and techniques of pretreatment for dilute acid hydrolysis and low temperature acid hydrolysis occur at temperature ranges of about 160 degrees Celsius and a range of eighty (80) degrees to one hundred (100) degrees Celsius, respectively. However, using the conventional methods, in order to begin the enzymatic hydrolysis and fermentation reactions, the pretreatment mixture/slurry needs to be cooled to around forty (40) degrees to fifty (50) degrees Celsius.

In contrast to the current and/or conventional methods, the HAMs incorporated into the organism may function to, assist in, and/or carry out the breakdown and/or hydrolysis of biomass and/or cellulosic materials into more simple sugar molecules and/or sugar monomers in a broad range of temperatures. Some non-limiting examples of temperature ranges include: at least about fifty (50) degrees Celsius; at least about seventy (70) degrees Celsius; from about forty-five (45) degrees Celsius to about eighty (80) degrees Celsius; from about eighty (80) degrees Celsius to about one hundred (100) degrees Celsius; from about eighty-five (85) degrees to about ninety-five (95) degrees Celsius; and/or from about ninety (90) degrees to about one hundred (100) degrees Celsius.

In embodiments, the one or more HAMs may be isolated from, derived from and/or originate from one or more organisms. The one or more organisms may comprise the same organism, organisms within the same genus and/or within the same species, and/or different and/or distinct organisms. In one non-limiting example, the HAMs are from one or more extremophiles, such as, but not limited to: hyperthermophilic, thermophilic, acidophilic, thermoacidophilic, and/or polyextremophilic organisms. Some non-limiting examples of organisms include: *Alicyclobacillus acidocaldarius; Clostridium thermocellum; Clostridium thermolacticum; Clostridium thermohydrosulfuricum; Trichoderma reesei*; a variety of *Bacillus* species (i.e., *B. subtilis, B. thermoamylovorans, B. stearothermophilus, B. granulobacter, B. pectinovorum, B. halodurans*, etc.); *Moorella thermoautotrophica; Moorella thermoacetica; Streptococcus (Lactobacillus) thermophilus*; and/or other extremophilic bacteria that possess one or more nucleic acids associated with the breakdown and/or hydrolysis of biomass and/or lignocellulosic material into more simple sugar molecules and/or sugar monomers. It is also contemplated that the HAMs may be isolated from, derived from, or otherwise originate from any type and/or kind of organism that includes one or more of the HAMs and/or other extremophilic bacteria that possess one or more nucleic acids encoding proteins involved in breakdown and/or hydrolysis of biomass and/or lignocellulosic material into products. It is also contemplated that the HAMs may be isolated from, derived from, or otherwise originate from any type and/or kind of organism that includes one or more of the HAMs, such as, but not limited to, those found online at wzw.tum.de/mbiotec/cellmo.htm; or available from an institution, such as, but not limited to, the Advanced Biotechnology Center (ABC) (Italy); Interlab Cell Line Collection (Biotechnology Dept.) (Italy); the Australian Government Analytical Laboratories (AGAL); the American Type Culture Collection (ATCC); the Belgian Coordinated Collections of Microorganisms (BCCM); the Prime Minister's Services Federal Office for Scientific, Technical and Cultural Affairs (OSTC) (Belgium); Bureau of Microbiology at Health Canada (BMHC); Centraalbureau voor Schimmelcultures (CBS) (the Netherlands); China Center for Type Culture Collection (CCTCC) (Wuhan); China Committee for Culture Collection of Microorganisms (Beijing); Coleccion Espafiola de Cultivos Tipo (CECT) (Spain); Collection Nationale De Cultures De Microorganismes (CNCM) (Institut Pasteur, France); Collection of Industrial Yeasts DBVPG (Perugia, Italy); Culture Collection of Algae and Protozoa (CCAP) (United Kingdom); Culture Collection of Yeasts (CCY) (Slovakia); Czech Collection of Microorganisms (CCM); Deutsche Sammlung von Mikroorganismen und Zellkulturen GmbH (DSMZ) (Germany); European Collection of Cell Cultures (ECACC) (United Kingdom); Institute of Agriculture and Food Biotechnology (IAFB) Collection of Industrial Microorganisms (Poland); International Mycological Institute (IMI) (United Kingdom); International Patent Organism Depositary (IPOD) (Tsukuba, Japan); Korean Cell Line Research Foundation (KCLRF); Korean Collection for Type Cultures (KCTC); Korean Culture Center of Microorganisms (KCCM); Microbial Strain Collection of Latvia (MSCL); National Bank for Industrial Microorganisms and Cell Cultures (NBIMCC) (Bulgaria); National Collection of Agricultural and Industrial Microorganisms (NCAIM) (Budapest, Hungary); National Collection of Type Cultures (NCTC) (United Kingdom); National Collection of Yeast Cultures (NCYC); AFRC Institute of Food Research (United Kingdom); National Collections of Industrial, Food and Marine Bacteria (NCIMB) (Scotland); National Research Center of Antibiotics (Moscow); Polish Collection of Microorganisms (PCM) (Poland); Russian Collection of Microorganisms (VKM); and the Russian National Collection of Industrial Microorganisms (VKPM) (Russia).

In embodiments, one or more of the HAMs may be incorporated into, integrated into, and/or otherwise expressed in one or more organisms that may already have the ability to ferment sugars to products. Such organisms may be any organism known in the art that has the ability to ferment sugars to alcohols or other products. A non-exhaustive list of organisms may include: *Clostridium thermocellum; Clostridium thermolacticum; Clostridium thermohydrosulfuricum*; a variety of *Bacillus* species (i.e., *B. subtilis, B. thermoamylovorans, B. stearothermophilus, B. granulobacter, B. pectinovorum, B. halodurans*, etc.); *Moorella thermoautotrophica; Moorella thermoacetica; Streptococcus (Lactobacillus) thermophilus; Saccharomyces cerevisiae* (yeast), *Zymomonas mobilis, Candida shehatae, E. coli*, those found at any of the web sites or institutions listed herein, and/or other organisms that possess one or more nucleic acids coding for proteins involved in fermentation of sugars to products.

It is additionally contemplated that the organism able to ferment sugars to products may be any organism that has nucleic acids encoding for one or more proteins involved with the fermentation pathways, such as, but not limited to, hexokinase I, hexokinase II, glucokinase, glucose-6-phosphate isomerase, phosphofructokinase, aldolase, triosephosphate isomerase, glyceraldehyde-3-phosphate dehydrogenase, 3-phosphoglycerate kinase, phosphoglycerate mutase, enolase, enolase I, pyruvate decarboxylase, citrate synthase, aconitase, isocitrate dehydrogenase, succinate dehydrogenase, fumarase, xylose reductase, xylitol dehydrogenase, xylulokinase, phosphoketolase, lactate dehydrogenase, acetyl-CoA-acetyl transferase, β-hydroxybutyryl-CoA dehydrogenase, crotonase, butyryl CoA dehydrogenase, phosphobutyrylase, butyrate kinase, and alcohol dehydrogenase. In embodiments of the present invention, the organism may already include those enzymes and/or nucleic acids encoding enzymes, necessary for fermenting sugars to products. Some non-limiting examples of these enzymes include: hexokinase I, hexokinase II, glucokinase, glucose-6-phosphate isomerase, phosphofructokinase, aldolase, triosephosphate isomerase, glyceraldehyde-3-phosphate dehydrogenase, 3-phosphoglycerate kinase, phosphoglycerate mutase, enolase, enolase I, pyruvate decarboxylase, citrate synthase, aconitase, isocitrate dehydrogenase, succinate dehydrogenase, fumarase, xylose reductase, xylitol dehydrogenase, xylulokinase, phosphoketolase, lactate dehydrogenase, acetyl-CoA-acetyl transferase, 3-hydroxybutyryl-CoA dehydrogenase, crotonase, butyryl CoA dehydrogenase, phosphobutyrylase, butyrate kinase, and alcohol dehydrogenase.

In embodiments, one or more of the HAMs may include and/or be expressed with one or more regulatory elements and/or proteins, such as, but not limited to, promoters, enhancers, transcription factors, activators, silencers, and/or so forth. Non-limiting examples of such regulatory elements may be found in the patent applications and patents previously incorporated herein by reference. In this manner, the transcription and/or expression of one or more of the HAMs may be regulated and/or controlled. In a non-limiting example, the HAMs may include a promoter region substantially similar to promoter regions of one or more of the organism's Fermentation Associated Molecules (FAMs) (those nucleic acids encoding proteins involved in the fermentation of sugars to products). In this manner, transcription and/or expression of one or more of the HAMs occur at substantially the same time, or substantially simultaneous with, the transcription and/or expression of one or more of the FAMs. It is also contemplated that one or more of the HAMs may be included and/or integrated under the control of the same promoter and/or promoter regions of the FAMs in one or more of the organisms. Some non-limiting examples of types of promoters contemplated include: constitutive promoters, tissue specific or development stage promoters, inducible promoters, and/or synthetic promoters. In one embodiment, the promoter may be a standard promoter used in expression vectors, such as, but not limited to, the T7 and Sp6 Phage promoters, which promote the expression of inserted nucleic acids in a phage type vector.

In embodiments, one or more of the HAMs may comprise and/or be included in a delivery system that may deliver, incorporate, transfer, and/or assist in the delivery and/or expression of one or more of the HAMs into one or more of the organisms able to break down and/or convert cellulose to more simple sugar molecules. The delivery system may comprise any method for incorporating DNA, nucleic acids and/or vectors in cells known in the art, such as but not limited to, transfection, electroporation, lipofection, transformation, gene guns, Biolistic Particle Delivery Systems, and/or so forth.

It is additionally contemplated that one or more HAMs may be incorporated into any type and/or kind of vector known in the art. A non-exhaustive list of potential vectors include: plasmids, bacteriophages, viruses, yeast artificial chromosomes (YACs) bacterial artificial chromosomes (BACs), P1 bacteriophage-derived chromosomes (PACs), mammalian artificial chromosomes, and/or so forth. The insertion and/or incorporation of desired nucleic acids into vectors is well understood, and in many instances vectors and/or insertion of nucleic acids into vectors are commercially available (i.e., through Empire genomics at empiregenomics.com/site/products_bacclones.php).

In embodiments, the delivery systems and/or vectors that may be used to incorporate one or more of the HAMs may include selective markers, tags, or the like. Such selective markers tags, etc., may enable the determination of a successful delivery, integration, and/or expression of a vector including one or more of the HAMs. Some non-limiting examples of selective markers, tags, etc., include: antibiotic resistance, amino acid/nutrient markers, color markers, fluorescent markers (i.e., GFP, RFP, etc.), His-tags, FLAG tags, Calmodulin-tags, HA-tags, Maltose binding protein-tags, Thioredoxin-tags, S-tags, Strep-tags, Nus-tags, and/or so forth.

In embodiments, it is contemplated that one or more of the HAMs may be integrated with, incorporated into, and/or become part of the genome and/or DNA of the host organism. Integrating one or more of the HAMs into the host DNA may provide for better expression, replication to subsequent host progeny, and/or protection from DNA degradation by the host organism. Numerous methods and/or vectors for integrating, inserting, and/or incorporating a desired nucleic acid into a host genome are well known in the art. A non-exhaustive list of potential vectors include: phage lambda (λ), adeno-associated virus (AAV), adenovirus, lentivirus, retroviruses, transposons, or the like. Additionally, a multipurpose vector system may be used as taught in Laitinen et al., A multi-purpose vector system . . . , *Nucleic Acids Research,* 2005, vol. 33, no. 4, which is incorporated by reference herein.

Expression/Integration of Fermentation Associated Molecules

In one embodiment of the invention one or more Fermentation Associated Molecules (FAMs), encoding for proteins associated with, involved in, and/or assisting in the fermentation of sugars to products may be incorporated and/or inserted into an organism that has the ability to break down lignocellulosic materials to more simple sugar molecules. The FAMs may include any nucleic acids, proteins and/or enzymes that are associated with the fermentation of sugars to products. A non-exhaustive list of these proteins and/or enzymes includes: hexokinase I, hexokinase II, glucokinase, glucose-6-phosphate isomerase, phosphofructokinase, aldolase, triosephosphate isomerase, glyceraldehyde-3-phosphate dehydrogenase, 3-phosphoglycerate kinase, phosphoglycerate mutase, enolase, enolase I, pyruvate decarboxylase, citrate synthase, aconitase, isocitrate dehydrogenase, succinate dehydrogenase, fumarase, xylose reductase, xylitol dehydrogenase, xylulokinase, phosphoketolase, lactate dehydrogenase, acetyl-CoA-acetyl transferase, β-hydroxybutyryl-CoA dehydrogenase, crotonase, butyryl CoA dehydrogenase, phosphobutyrylase, butyrate kinase, and alcohol dehydrogenase.

In additional embodiments, the FAMs encompass all those nucleic acids coding for proteins associated with the replication, transcription, translation, and/or expression of nucleic acids associated with the fermentation of sugars to a product. In a non-limiting example, FAMs may comprise those nucleic acids constituting either regulatory sequences or coding for proteins involved with the regulation of FAMs, such as, but not limited to, those nucleic acid sequences and/or proteins that increase replication, transcription, expression, etc., of FAMs. Further, FAMs may comprise those nucleic acids that are involved with the down-regulation of FAMs, either directly or through the proteins they may encode. A non-exhaustive list of proteins encoded by these FAMs may include: transcription factors, enhancers, repressors, DNA binding proteins, or the like.

In further embodiments, the FAMs may include derivatives, analogs, and/or modified versions of one or more FAMs. These derivatives, analogs, and/or modified versions may include those modifications carried out either in vive or in vitro. Some non-limiting examples of derivatives, analogs, and/or modifications include: substitutions, deletions, mutations, modifications, etc. Modifications may comprise all modifications occurring to nucleic acids, DNA, RNA, proteins, etc., such as, but not limited to, acetylation, deacetylation, alkylation, methylation, demethylation, carboxylation, glycosylation, phosphorylation, hydroxylation, PEGylation, biotinylation, and/or any other type of modification known in the art.

In yet other embodiments, the FAMs may encompass those nucleic acids, regulatory sequences, proteins, and/or enzymes which are encoded by the FAMs that are derivatives of FAMs and/or include tags, markers, and/or other modifications. A non-exhaustive list of tags may include: His-tags, FLAG tags, Calmodulin-tags, HA-tags, Maltose binding protein-tags, Thioredoxin-tags, S-tags, Strep-tags, Nus-tags, or the like. The FAMs may also include those nucleic acids, proteins, and/or enzymes that include fluorescent markers, such as, but not limited to, GFP, RFP, YFP, BFP, or the like.

Advantageously, the incorporation of the FAMs into the one or more organisms with the ability to break down biomass to more simple sugar molecules may enable the one or more genetically modified organisms to convert lignocellulose and/or other biomass materials more efficiently into a product under a variety of pH and/or temperature conditions. In one embodiment, the one or more genetically modified organisms may carry out the biomass conversion in a range of pH conditions from at or less than a pH of about 7; at or less than a pH of about 5, from about a pH of 1 to about a pH of 5, and/or from about a pH of 1 to about a pH of 1.3.

Advantageously, in one embodiment, the ability of the genetically modified organism to function and/or convert biomass into products at pH conditions of 1 to 5, eliminates the need to neutralize and/or increase the pH to a range of about 5 to 6.0 for enzymatic hydrolysis and fermentation, which, using conventional methods, is necessary for the hydrolysis and fermentation of cellulose to products. Indeed, in conventional methods of dilute acid hydrolysis, the pretreatment hydrolysate needs to be neutralized to enable enzymatic hydrolysis and fermentation to occur. As such, in one embodiment, the FAMs may code for enzymes which comprise thermophilic, thermoacidophilic, and/or acidophilic properties and/or characteristics, or in the alternative may be derived from, analogs of, and/or homologues of one or more thermophilic, thermoacidophilic, and/or acidophilic FAMs from other organisms.

It is additionally contemplated that one or more of the proteins encoded by the FAMs may function and/or have an optimum pH range of above a pH of 5. Indeed, one or more of the proteins encoded by the FAMs may function and/or enable fermentation of sugar to products in pH conditions that range from a pH of about 5 to a pH of about 14.

In still another embodiment, enzymes encoded by one or more FAMs may function to and/or assist in fermenting sugars to products in a broad range of temperatures. Conventional methods and techniques of pretreatment using dilute acid hydrolysis and low temperature acid hydrolysis occur at temperature ranges of about 160 degrees Celsius and a range of eighty (80) degrees to one hundred (100) degrees Celsius, respectively. However, using the conventional methods, in order to begin the enzymatic hydrolysis and fermentation reactions, the pretreatment mixture/slurry needs to be cooled to around forty (40) degrees to fifty (50) degrees Celsius.

In contrast to the current and/or conventional methods, the FAMs incorporated into one or more of the organisms described herein may function to, assist in, and/or carry out the fermentation process in a broad range of temperatures. Some non-limiting examples of temperature ranges include: at least about fifty (50) degrees Celsius, at least about seventy (70) degrees Celsius, from about forty-five (45) degrees Celsius to about eighty (80) degrees Celsius; from about eighty (80) degrees Celsius to about one hundred (100) degrees Celsius; from about eighty-five (85) degrees to about ninety-five (95) degrees Celsius; and/or from about ninety (90) degrees to about one hundred (100) degrees Celsius.

In further embodiments, the one or more FAMs may be isolated from, derived from and/or originate from one or more organisms. The one or more organisms may comprise the same organism, organisms within the same genus and/or within the same species, and/or different and/or distinct organisms. In one non-limiting example, the FAMs are from one or more extremophiles, such as, but not limited to: hyperthermophilic, thermophilic, acidophilic, thermoacidophilic, and/or polyextremophilic organisms. Some non-limiting examples of organisms include: *Alicyclobacillus acidocaldarius, Clostridium thermocellum; Clostridium thermolacticum; Clostridium thermohydrosulfuricum*; a variety of *Bacillus* species (i.e., *B. subtilis, B. thermoamylovorans, B. stearothermophilus, B. granulobacter B. pectinovorum, B. halodurans*, etc.); *Moorella thermoautotrophica; Moorella thermoacetica; Streptococcus (Lactobacillus) thermophilus*, those found at any of the web sites or institutions listed herein, and/or other organisms that possess one or more nucleic acid sequences involved in fermentation of sugars to products. It is also contemplated that the FAMs may be isolated from, derived from, or otherwise originate from non-extremophilic organisms, such as, but not limited to, *Saccharomyces cerevisiae* (yeast), *Zymomonas mobilis, Candida shehatae, E. coli*, and/or other organisms which possess one or more nucleic acids involved in fermentation of sugars to products.

In embodiments, one or more of the FAMs may be incorporated into, integrated into, and/or otherwise expressed in one or more organisms that already have the ability to break down lignocellulose and/or biomass to more simple sugar molecules. Such organisms may be any organism known in the art that has the ability to break down lignocellulose to more simple sugar molecules. A non-exhaustive list of such organisms may include: *Alicyclobacillus acidocaldarius; Clostridium thermocellum; Clostridium thermohydrosulfuricum*; and/or any other organism that is known to have the ability to break down lignocellulose and/or biomass. It is additionally contemplated that the organism able to break down lignocellulose and/or biomass may be any organism that has nucleic acid sequences encoding one or more types of endo- and/or exo-cellulases, i.e., endo-beta-1,4-glucanase; one or more types of hemicellulases, i.e., endo-beta-1,4-xylanase; and/or one or more xylosidase enzymes.

In one embodiment of the present invention, an organism may already include enzymes and/or nucleic acids encoding enzymes, for breaking down at least one of the three major components of lignocellulose: cellulose, hemicellulose, and lignin. Some non-limiting examples of these enzymes include endo- and/or exo-β-1,4-glucanases. The endo- and/or exo-β-1,4-glucanases may function to hydrolyze the linked glucose residues (endo activity) and/or hydrolyze the ends of the cellulose polymers (exo activity). Additionally, the organism may already include endo-β-1,4-xylanase; and/or one or more xylosidase enzymes, such enzymes possessing the ability to hydrolyze one or more types of hemicellulose polymers. In an additional embodiment, the organism may include additional and/or accessory enzymes, proteins, or nucleic acid sequences that may assist in completely hydrolyzing, transporting, metabolizing and/or breaking down the one or more types of lignocellulose polymers into more simple sugar molecules and/or sugar monomers.

In embodiments, it is contemplated that the organism may include one or more enzymes and/or nucleic acids encoding enzymes that have the ability to break down, transport, metabolize, and/or hydrolyze lignin molecules; including nucleic acids encoding for ligninolytic enzymes such as manganese peroxidase, laccase, lignin peroxidase, or the like.

In embodiments, one or more of the FAMs may include and/or be expressed with one or more regulatory factors, regulatory elements, and/or proteins, such as, but not limited to, promoters, enhancers, transcription factors, activators, silencers, and/or so forth. Non-limiting examples of such regulatory elements may be found in the patent applications and patents previously incorporated herein by reference. In this manner, the transcription and/or expression of one or more of the FAMs may be regulated and/or controlled. In a non-limiting example, the FAMs may include a promoter region substantially similar to promoter regions of one or more of the organism's Hydrolysis Associated Molecules (HAMs) (those nucleic acids involved in breaking down lignocellulosic materials to simpler sugars). In this manner, transcription and/or expression of one or more of the FAMs occur at substantially the same time, or substantially simultaneous with, the transcription and/or expression of the Hydrolysis Associated Molecules. It is also contemplated one or more of the FAMs may be included and/or integrated under the control of the same promoter and/or promoter regions of the Hydrolysis Associated Molecules in one or more of the organisms. Some non-limiting examples of types of promoters contemplated include: constitutive promoters, tissue specific or development stage promoters, inducible promoters, and/or synthetic promoters. In one embodiment, the promoter may be a standard promoter used in expression vectors, such as, but not limited to, the T7 and Sp6 Phage promoters, which promote the expression of inserted nucleic acids in a phage type vector.

In embodiments, one or more of the FAMs may comprise and/or be included in a delivery system that may deliver, incorporate, transfer, and/or assist in the delivery and/or expression of one or more of the FAMs into one or more of the organisms able to break down and/or convert lignocellulose to more simple sugar molecules. The delivery system may comprise any method for incorporating DNA, nucleic acids and/or vectors into cells known in the art. A non-exhaustive list of methods may include: transfection, electroporation, lipofection, transformation, gene guns, Biolistic Particle Delivery System, and/or so forth.

It is additionally contemplated that one or more FAMs may be incorporated into any type and/or kind of vector known in the art. A non-exhaustive list of potential vectors include: plasmids, bacteriophages, viruses, yeast artificial chromosomes (YACs), bacterial artificial chromosomes (BACs), P1 bacteriophage-derived chromosomes (PACs), mammalian artificial chromosomes, and/or so forth. The insertion and/or incorporation of desired nucleic acids into vectors is well understood in the art, and in many instances vectors and/or insertion of nucleic acids into vectors are commercially available (i.e., through Empire genomics empiregenomics.com/site/products_bacclones.php).

In embodiments, the delivery systems and/or vectors that may be used to incorporate one or more of the FAMs may include and/or encode selective markers, tags, or the like, that may enable the determination of a successful delivery, integration, and/or expression of a vector including one or more of the FAMs. Some non-limiting examples of selective markers, tags, etc., include: antibiotic resistance, amino acid/nutrient markers, color markers, fluorescent markers (i.e., GFP, RFP, etc.), His-tags, FLAG tags, Calmodulin-tags, HA-tags, Maltose binding protein-tags, Thioredoxin-tags, S-tags, Strep-tags, Nus-tags, and so forth.

In embodiments, it is contemplated that one or more of the FAMs may be integrated with, incorporated into, and/or become part of the genome and/or DNA of the host organism. Integrating one or more of the FAMs into the host DNA may provide for better expression, replication to subsequent host progeny, and/or protection from DNA degradation by the host organism. There are numerous methods and/or vectors for integrating, inserting, and/or incorporating a desired nucleic acid into a host genome which are well known in the art. A non-exhaustive list of potential vectors include: phage lambda (λ), adeno-associated virus (AAV), adenovirus, lentivirus, retroviruses, transposons, or the like. Additionally, a multipurpose vector system may be used as taught in Laitinen et al., A multi-purpose vector system . . . , *Nucleic Acids Research*, 2005, vol. 33, no. 4, which is incorporated by reference herein.

BioProcessing

In embodiments, one or more of the genetically modified organisms described herein may produce one or more proteins from the FAMs and/or HAMs intracellularly and/or extracellularly. In producing proteins extracellularly, the genetically modified organism may excrete the proteins, enzymes, etc., into the extracellular and/or surrounding environment. It is additionally contemplated that the outer membrane and/or cell wall of the genetically modified organism may be coated with and/or include one or more proteins encoded by the HAMs. In this manner, breakdown and/or hydrolysis of biomass/lignocellulosic material is realized in the extracellular environment.

In embodiments, one or more of the genetically modified organisms described herein may convert biomass and/or lignocellulosic material to products at least partially intracellularly, or otherwise internal to the genetically modified organism. In a non-limiting example, at least partially hydrolyzed sugar molecules may be brought and/or transported into the genetically modified organism and fermented to ethanol or another product. The one or more genetically modified organism may then excrete the ethanol or other product into the extracellular environment.

It is contemplated that one more of the genetically modified organisms described herein may have multiple methods of use, uses, and/or applications in a wide variety of industries, laboratories, markets, etc.

In embodiments, one or more of the genetically modified organisms described herein may be applied to biomass and/or lignocellulosic material such that the biomass and/or lignocellulosic material is broken down, depolymerized, and subsequently converted to products. The one or more genetically modified organisms may be applied to the biomass or lignocellulosic material/composition in any manner known in the art. In a non-limiting example, the biomass and/or lignocellulosic material may be ground up and/or undergo a grinding process. Additionally, the biomass and/or lignocellulosic material may undergo various pretreatments prior to exposure to the recombinant organism. Such treatments may include, but are not limited to, sulfur dioxide, steam explosion, acid hydrolysis, ammonia hydrolysis, autohydrolysis, or the like. Additional, non-limiting examples are described in Thomas et al., which is incorporated by reference herein.

In embodiments, one or more of the genetically modified organisms described herein may be applied to biomass and/or lignocellulosic material, such as, but not limited to, cellulose, through the use of multiple methods and/or procedures. In one non-limiting example, a lignocellulosic composition may comprise one or more solid substrates/phases which are inoculated with the one or more genetically modified organisms, and/or cultures thereof. Additionally, the lignocellulosic composition may be embodied in a liquid, or substantially liquid substrate/phase; and the one or more genetically modified organisms introduced therein.

In embodiments, it is additionally contemplated that enzymes and/or proteins encoded by any and/or all of the HAMs and/or FAMs may be extracted, removed and/or isolated from one or more genetically modified organisms described herein. These enzymatic and/or proteinaceous compositions may then be applied to biomass and/or lignocellulosic material.

In embodiments, the biomass and/or lignocellulosic composition is inoculated with a genetically modified organism culture. It is contemplated there may be a variety of conditions (i.e., pH, concentrations of biomass and/or lignocellulosic material, concentration of genetically modified organisms, temperature, pressure, etc.) at which hydrolysis of the biomass and/or lignocellulosic material and subsequent fermentation may occur. Indeed, the pH of the hydrolysis may include ranges of at or less than a pH of about 7; at or less than a pH of about 5; about a pH of 1 to about a pH of 5; and/or from about a pH of 1 to about a pH of 1.3.

In embodiments, the ability of the one or more hydrolysis and/or fermentation reactions occurring in pH conditions of 1 to 5, may eliminate the need to neutralize and/or increase the pH to a range of about 5 to 6 following acid pretreatment for enzymatic hydrolysis and fermentation that, using conventional methods, is necessary for the hydrolysis and fermentation of lignocellulosic material to products. Indeed, in conventional methods of dilute acid hydrolysis, the pretreatment hydrolysate needs to be neutralized to enable enzymatic hydrolysis and fermentation to occur. As such, in one embodiment, the HAMs may code for enzymes that comprise thermophilic, thermoacidophilic, and/or acidophilic properties and/or characteristics, or in the alternative may be derived from one or more thermophilic, thermoacidophilic, and/or acidophilic organisms.

It is additionally contemplated that one or more hydrolysis and/or fermentation reactions may occur and/or have an optimum pH range of above a pH of 5. Indeed, the hydrolysis and/or fermentation reactions may occur in pH conditions that range from a pH of about 5 to a pH of about 14.

In embodiments, the one or more hydrolysis and/or fermentation reactions may occur in a broad range of temperatures. Some non-limiting examples of temperature ranges include: from about fifty (50) degrees Celsius; from about seventy (70) degrees Celsius; from about eighty (80) degrees Celsius to about one hundred (100) degrees Celsius; from about eighty-five (85) degrees to about ninety-five (95) degrees Celsius; and/or from about ninety (90) degrees to about one hundred (100) degrees Celsius.

In embodiments, one or more of the genetically modified organisms described herein may be grown and/or cultured in accordance with known methods. Such genetically modified organism cultures may be fluidly applied and/or contacted with biomass and/or lignocellulosic compositions, such as, but not limited to, polysaccharides, cellulose, lignocellulose, hemicellulose, lignin, starch, sugars, sugar oligomers, carbohydrates, complex carbohydrates, chitin, heteroxylans, glycosides, xylan-, glucan-, galactan-, or mannan-decorating groups.

In embodiments, cellular and/or proteinaceous extracts of the genetically modified organism cultures may be isolated. Protein and/or cellular isolations and extractions may be conducted through conventional methods. The cellular and/or proteinaceous extracts may be applied to and/or contacted with the biomass and/or lignocellulosic compositions as described herein.

In embodiments, one or more of the genetically modified organisms and/or one or more of the cellular and/or proteinaceous extracts described herein may be applied and/or fluidly contacted with biomass and/or lignocellulosic compositions under thermophilic, acidophilic, and/or thermoacidophilic conditions. In a non-limiting example, the temperature may be at or above about fifty (50) degrees and/or the pH at or below about the pH of 5 in a treatment mixture, slurry, apparatus or other area in which the fluid application occurs.

It is contemplated that a variety of conventional methods and/or techniques may be used to create the one or more genetically modified organisms described herein. One non-limiting method is described in U.S. Pat. No. 4,624,922, which is incorporated by reference herein.

Integration of Pretreatment, Biological Processing, and Product Recovery

Typically, the fermentative biological production of products from biomass proceeds through four distinct steps: pretreatment, cellulolytic hydrolysis, fermentation, and recovery. The pretreatment and recovery steps remain distinct in typical process designs, while the cellulolytic hydrolysis and fermentations steps can be separate steps or can be combined in various ways.

The pretreatment step is typically a physical or chemical pretreatment, such as an acid pretreatment, that effects a modification of the biomass to aid in further processing with cellulase enzymes. Typically, after a suitable period, the acid of the pretreatment is neutralized before initiating cellulolytic hydrolysis. In the most basic processing configuration, cellulolytic hydrolysis is carried out using exogenously added enzymes and is carried out separately from the fermentation step (separate hydrolysis and fermentation, or SHF). Glucose generated from the cellulose during cellulolytic hydrolysis, and pentose sugars released during the pretreatment, are separately consumed by fermenting organism(s) that are introduced to ferment the simple sugars into ethanol or another product of value. After fermentation, the product is recovered in a recovery step.

Additional processing configurations are typically utilized in which the cellulolytic hydrolysis using exogenously added enzymes and fermentation steps may be integrated. These include separate cellulolytic hydrolysis followed by co-fermentation of the pentose and hexose sugars (separate hydrolysis and co-fermentation, or SHCF), simultaneous cellulolytic hydrolysis and glucose fermentation (simultaneous saccharification and fermentation, or SSF) with separate pentose fermentation, simultaneous cellulolytic hydrolysis and co-fermentation of the glucose and pentose sugars (simultaneous saccharification and co-fermentation, or SSCF).

A final processing configuration can be used in which the organism utilized to ferment glucose released during cellulolytic hydrolysis serves as the source of the cellulolytic enzymes. In this configuration, a physical and/or chemical pretreatment is utilized to improve the action of the endogenously produced cellulolytic enzymes on the cellulose. This processing configuration is referred to as Consolidated Bioprocessing (CBP).

In embodiments of the invention, the above schemes may be modified through the use of enzymes and/or organisms active and stable at increased temperatures and decreased pH to allow the combination of pretreatment and/or product recovery with the conventional biological processing steps. In certain embodiments, the pretreatment may be conducted at lowered temperatures relative to existing dilute acid pretreatment technology and this step may be carried out enzymatically utilizing thermoacidophilic lignocellulose-degrading enzymes. The altered pretreatment and subsequent biological processing (cellulolytic hydrolysis and fermentation) may be carried out sequentially or combined together. The pretreatment and biological processing, may, in certain embodiments, be carried out by isolated enzymes and/or organisms for the cellulolytic hydrolysis and/or fermentation steps according to the present invention. The enzymes may be added exogenously or may be produced by the fermentation organisms in a Combined Pretreatment and Consolidated Bioprocessing (CPBP) configuration. In certain embodiments, the thermoacidophilic enzymes and organisms may include *Alicyclobacillus acidocaldarius*, genetically modified organisms comprising one or more nucleotides sequences derived or isolated from *Alicyclobacillus acidocaldarius*, or by extracts and/or lysates comprising one or more proteins produced by or derived from *Alicyclobacillus acidocaldarius*. In embodiments, the pretreatment step may comprise an acid pretreatment; alkaline pretreatment; hydrothermal pretreatment; and/or an organosolvent pretreatment.

In further embodiments, the acid or alkali added to or generated during a pretreatment step may not need to be neutralized before hydrolysis and/or fermentation. In embodiments, the non-neutralization of the pretreatment conditions may lead to the decreased function or death of any unwanted organisms present on the incoming biomass to be treated. In embodiments, the non-neutralization of the pretreatment conditions may result in decreased byproducts or unwanted products as the function of any unwanted organisms present on the incoming biomass to be treated may be decreased.

In additional embodiments, one or more genetically modified organisms, HAMs, and/or FAMs according to the present invention may play a role in the pretreatment, cellulolytic hydrolysis, and fermentation, or in any combination thereof. For example, a genetically modified organism according to the present invention may carry out processes contributing to pretreatment and cellulolytic hydrolysis, and a second genetically modified organism according to the present invention may separately or simultaneously carry out the fermentation. In another non-limiting example, thermoacidophilic enzymes according to the present invention may carry out processes contributing to pretreatment, and one or more genetically modified organism(s) according to the present invention may carry out processes contributing to cellulolytic hydrolysis and/or fermentation. In a further non-limiting example, a single genetically modified organism(s) according to the present invention may carry out processes contributing to pretreatment, cellulolytic hydrolysis, and fermentation.

In embodiments, a reduced severity acid pretreatment step may be combined with, or occur sequentially with, the addition of thermoacidophilic lignocellulose-degrading enzymes, and occur separately or concurrently with one or both of the cellulolytic hydrolysis and fermentation steps.

Expression/Integration of Hydrolysis Associated Molecules and Fermentation Associated Molecules In embodiments of the invention one or more Hydrolysis Associated Molecules (HAMs) and/or one or more Fermentation Associated Molecules (FAMs) may be incorporated and/or inserted into an organism.

The incorporation of the HAMs and FAMs into the one or more organisms may enable the one or more organisms to convert lignocellulosic and/or other biomass materials into a product at a variety of pH and temperature conditions. In one embodiment, the one or more genetically modified organisms may carry out the biomass conversion in a range of pH conditions from at or less than a pH of about 7; at or less than a pH of about 5; about a pH of 1 to about a pH of 5; and/or from about a pH of 1 to about a pH of 1.3.

In embodiments, the ability of the organism(s) to function and/or convert biomass into products in pH conditions of 1 to 5, may eliminate the need to neutralize and/or increase the pH to a range of about 5 to 6 for enzymatic hydrolysis and/or fermentation after dilute acid pretreatment, which, using conventional methods, is necessary for the hydrolysis and fermentation of cellulose to products. Indeed, in conventional methods of dilute acid hydrolysis, the pretreatment hydrolysate needs to be neutralized to enable enzymatic hydrolysis and fermentation to occur. As such, in one embodiment, the HAMs and FAMs may code for or be enzymes that possess thermophilic, thermoacidophilic, and/or acidophilic properties and/or characteristics, or in the alternative may be derived from one or more thermophilic, thermoacidophilic, and/or acidophilic organisms.

It is additionally contemplated that one or more of the HAMs and FAMs may function and/or have an optimum pH range of above a pH of 5. Indeed, one or more of the HAMs and FAMs may function and/or enable breakdown and/or hydrolysis of biomass and/or lignocellulosic material into products in pH conditions that range from a pH of about 5 to a pH of about 14.

Conventional methods and techniques of pretreatment for dilute acid hydrolysis and low temperature acid hydrolysis occur at temperature ranges of about 160 degrees Celsius and a range of eighty (80) degrees to one hundred (100) degrees Celsius, respectively. However, using the conventional methods, in order to begin the enzymatic hydrolysis and fermentation reactions, the pretreatment mixture/slurry needs to be cooled to around forty (40) degrees to fifty (50) degrees Celsius.

In contrast to the current and/or conventional methods, the HAMs and FAMs may function to, assist in, and/or carry out the breakdown and/or hydrolysis of biomass and/or lignocellulose into products in a broad range of temperatures. Some non-limiting examples of temperature ranges include: at least about fifty (50) degrees Celsius; at least about seventy (70) degrees Celsius; from about forty-five (45) degrees Celsius to about eighty (80) degrees Celsius; from about eighty (80) degrees Celsius to about one hundred (100) degrees Celsius; from about eighty-five (85) degrees to about ninety-five (95) degrees Celsius; and/or from about ninety (90) degrees to about one hundred (100) degrees Celsius).

In embodiments, the one or more HAMs and FAMs may be isolated from, derived from and/or originate from one or more organisms. The one or more organisms may comprise the same organism, organisms within the same genus and/or within the same species, and/or different and/or distinct organisms. In one non-limiting example, the HAMs and FAMs are from one or more extremophiles, such as, but not limited to: hyperthermophilic, thermophilic, acidophilic, thermoacidophilic, and/or polyextremophilic organisms. Some non-limiting examples of organisms include: *Alicyclobacillus acidocaldarius; Clostridium thermocellum; Clostridium thermolacticum; Clostridium thermohydrosulfuricum; Trichoderma reesei*; a variety of *Bacillus* species (i.e., *B. subtilis, B. thermoamylovorans, B. stearothermophilus, B. granulobacter B. pectinovorum, B. halodurans*, etc.); *Moorella thermoautotrophica; Moorella thermoacetica; Streptococcus* (*Lactobacillus*) *thermophilus*; and/or other extremophilic organisms that possess one or more nucleic acids encoding proteins involved in breakdown and/or hydrolysis of biomass and/or lignocellulosic material and fermentation of sugars into products. It is also contemplated that the HAMs and FAMs may be isolated from, derived from, or otherwise originate from any type and/or kind of organism that includes one or more of the HAMs and FAMs, such as, but not limited to, those found at any of the web sites or institutions listed herein.

In embodiments, one or more of the HAMs and FAMs may be incorporated into, integrated into, and/or otherwise expressed in one or more organisms that do not have the ability to break down and/or hydrolyze biomass and/or lignocellulose and/or ferment sugars to products. Such organisms may be any organism known in the art, such as, but not limited to, *E. coli, Thermus thermophilus*, and/or any other suitable organism known in the art.

In embodiments, one or more of the HAMs and FAMs may include and/or be expressed with one or more regulatory elements and/or proteins, such as, but not limited to, promoters, enhancers, transcription factors, activators, silencers, and/or so forth. Non-limiting examples of such regulatory factors may be found in the patent applications and patents previously incorporated herein by reference. In this manner, the transcription and/or expression of one or more of the HAMs and FAMs may be regulated and/or controlled. In a non-limiting example, the HAMs and FAMs may include a promoter region substantially similar to promoter regions of one or more of the organism's Fermentation Associated Molecules (those nucleic acids involved in the fermentation of sugars to products). In this manner, transcription and/or expression of one or more of the HAMs and FAMs occur at substantially the same time, or substantially simultaneous with, the transcription and/or expression of the endogenous FAMs.

It is also contemplated that one or more of the HAMs and FAMs may be included and/or integrated under the control of the same promoter and/or promoter regions in one or more of the organisms. Some non-limiting examples of types of promoters contemplated include: constitutive promoters, tissues specific or development stage promoters, inducible promoters, and/or synthetic promoters. In one embodiment, the promoter may be a standard promoter used in expression vectors, such as, but not limited to, the T7 and Sp6 Phage promoters, which promote the expression of inserted nucleic acids in a phage type vector.

In embodiments, one or more of the HAMs and FAMs may comprise and/or be included in a delivery system that may deliver, incorporate, transfer, and/or assist in the delivery and/or expression of one or more of the HAMs and FAMs into one or more organisms. The delivery system may comprise any method for incorporating DNA, nucleic acids and/or vectors in cells known in the art, such as, but not limited to, transfection, electroporation, lipofection, transformation, gene guns, Biolistic Particle Delivery Systems, and/or so forth.

It is additionally contemplated that one or more HAMs and FAMs may be incorporated into any type and/or kind of vector known in the art. A non-exhaustive list of potential vectors include: transposons, plasmids, bacteriophages, viruses, yeast artificial chromosomes (YACs), bacterial artificial chromosomes (BACs), P1 bacteriophage-derived chromosomes (PACs), mammalian artificial chromosomes, and/or so forth. The insertion and/or incorporation of desired nucleic acids into vectors is well understood in the art, and in many instances vectors and/or insertion of nucleic acids into vectors are commercially available (i.e., through Empire genomics at empiregenomics.com/site/products-_bacclones.php).

In embodiments, the delivery systems and/or vectors that may be used to incorporate one or more of the HAMs and FAMs may include selective markers, tags, or the like. Such selective marker and/or tags may enable the determination of successful delivery, integration, and/or expression of a vector including one or more of the HAMs and FAMs. Some non-limiting examples of selective markers, tags, etc., include: antibiotic resistance, amino acid/nutrient markers, color markers, fluorescent markers (i.e., GFP, RFP, etc.), His-tags, FLAG tags, Calmodulin-tags, HA-tags, Maltose binding protein-tags, Thioredoxin-tags, S-tags, Strep-tags, Nus-tags, and/or so forth.

In embodiments, it is contemplated that one or more of the HAMs and FAMs may be integrated with, incorporated into, and/or become part of the genome and/or DNA of the host organism. Integrating one or more of the HAMs and FAMs into the host DNA may provide for better expression, replication to subsequent host progeny, and/or protection from DNA degradation by the host organism. Numerous methods and/or vectors for integrating, inserting, and/or incorporating a desired nucleic acid into a host genome are well known in the art. A non-exhaustive list of potential vectors include: phage lambda ($\lambda$), adeno-associated virus (AAV), adenovirus, lentivirus, retroviruses, transposons, or the like. Additionally, a multipurpose vector system may be used as taught in Laitinen et al., 2005, A multi-purpose vector system . . . , *Nucleic Acids Research*, vol. 33, no. 4, which is incorporated by reference herein.

EXAMPLES

Example 1: Delivery/Expression of Fermentation Associated Molecules in *Alicyclobacillus acidocaldarius*

Nucleic acids encoding enzymes involved in the fermentation of sugars (i.e., glucose, xylose, galactose, arabinose, mannose, etc.) to products are provided to and subsequently expressed in *Alicyclobacillus acidocaldarius* using conventional molecular cloning techniques. Nucleic acids to be provided include those nucleic acids encoding for the proteins involved in the pathways that convert sugars to a product (FAMs). A non-exhaustive list of these proteins include: hexokinase I, hexokinase II, glucokinase, glucose-6-phosphate isomerase, phosphofructokinase, aldolase, triosephosphate isomerase, glyceraldehyde-3-phosphate dehydrogenase, 3-phosphoglycerate kinase, phosphoglycerate mutase, enolase, enolase I, pyruvate decarboxylase, citrate synthase, aconitase, isocitrate dehydrogenase, succinate dehydrogenase, fumarase, xylose reductase, xylitol dehydrogenase, xylulokinase, phosphoketolase, lactate dehydrogenase, acetyl-CoA-acetyl transferase, β-hydroxybutyryl-CoA dehydrogenase, crotonase, butyryl CoA dehydrogenase, phosphobutyrylase, butyrate kinase, and alcohol dehydrogenase. The FAMs may comprise nucleic acids from a wide variety of organisms that use fermentation pathways. Some non-limiting examples of these organisms include: *Saccharomyces cerevisiae* (yeast); *Clostridium thermocellum; Clostridium thermohydrosulfuricum*; a variety of *Bacillus* species (i.e., *B. subtilis, B. thermoamylovorans, B. stearothermophilus, B. granulobacter, B. pectinovorum, B. halodurans*, and/or so forth); *Alicyclobacillus acidocaldarius; Clostridium thermolacticum; Trichoderma reesei; Moorella thermoautotrophica; Moorella thermoacetica; Streptococcus (Lactobacillus) thermophilus*; and/or those found at any of the web sites or institutions listed herein.

Example 1(a): Delivery of FAMs Via a Transpososome

A transpososome is constructed to include nucleic acids encoding proteins involved in fermentation of sugars, or FAMs. Included in the transpososome are the nucleic acids necessary for insertion of the transposon, copies of the MuA transposase, Mu transposon ends, and provision for expression of the FAMs included in the transpososome in the particular organism in which they are to be utilized. Transpososomes may also be constructed using sequences and elements optimized for use in gram-positive bacteria. See, Pajunen et al., *Microbiology* (2005) 151, 1209-1218. Conventional techniques may be used to construct the transpososome. Additionally, the construction and/or insertion of desired nucleic acids into transpososomes is well known in the art, see, Pajunen et al. It is contemplated that multiple transpososomes may be constructed with FAMs and may include a variety of promoters, enhancers that may function to enhance and/or regulate expression of FAMs.

Once constructed, the transpososomes are introduced into *Alicyclobacillus acidocaldarius*. Transpososome constructs may be introduced into *A. acidocaldarius* by electroporation, and so forth. Such techniques are known in the art and are detailed in Sambrook J. C., E. F. Fritsch, and T. Maniatas, 1989. *Molecular Cloning: A Laboratory Manual*, 2nd ed., Cold Spring Harbor Laboratory Press, N.Y., pp. 6.3-6.34; or Sambrook and Russell, *Molecular Cloning: A Laboratory Manual* (3-*Volume Set*), $3^{rd}$ ed. (available online at molecularcloning.com/); both references incorporated by reference herein.

Example 2: Delivery/Expression of Hydrolysis Associated Molecules into an Organism Able to Ferment Sugar to Ethanol Nucleic acids encoding enzymes involved in the hydrolysis, or breakdown, of lignocellulosic materials (i.e., biomass, cellulose, hemicellulose, etc.) to simpler sugars (Hydrolysis Associated Molecules (HAMs)) are genetically introduced by conventional molecular cloning techniques into organisms that ferment sugars to ethanol and subsequently expressed therein. HAMs to be provided include those nucleic acids coding for the proteins involved in the pathways that break down or hydrolyze cellulose, hemicellulose, etc., to more simple sugar molecules. A non-exhaustive list of these proteins include: esterases of the alpha-beta hydrolase superfamily; alpha-beta hydrolase; alpha-glucosidases; alpha-xylosidase; alpha-L-arabinofuranosidase; altronate hydrolase; a cellulose/endoglucanase; a cellulase/endoglucanase; a polygalacturonase; an alpha-galactosidase; a cellobiose phosphorylase; a glycogen debranching enzyme; an acetyl esterase/acetyl hydrolase; a beta-1,4-xylanase; a cinnamoyl ester hydrolase; a carboxylesterase type B; a beta-galactosidase/beta-glucuronidase; a xylan alpha-1,2-glucuronidase; a 3-hydroxyisobutyryl-CoA hydrolase; a beta-glucosidase B-related glycosidase; and/or a chitooligosaccharide deacetylase, or as described herein. The HAMs may comprise nucleic acids from a wide variety of organisms that are able to hydrolyze and/or break down lignocellulosic material to more simple sugar molecules.

Example 2(a): Delivery of HAMs Via a Transpososome

A transpososome is constructed to include nucleic acids encoding proteins involved in hydrolysis or breakdown of lignocellulosic polymers, or HAMs. Included in the transpososome are the nucleic acids necessary for insertion of the transposon, copies of the MuA transposase, Mu transposon ends, and provision for expression of the HAMs included in the transpososome in the particular organism in which they are to be utilized. Transpososomes may also be constructed using sequences and elements optimized for use in gram-positive bacteria. See, Pajunen et al., *Microbiology* (2005) 151, 1209-1218. Conventional techniques may be used to construct the transpososome. Additionally, the construction and/or insertion of desired nucleic acids into transpososomes is well known in the art, see, Pajunen et al. It is contemplated that multiple transpososomes may be constructed with HAMs and may include a variety of promoters, enhancers that may function to enhance and/or regulate expression of HAMs.

Once constructed, the transpososomes are introduced into an organism that is able to ferment and/or convert sugar molecules to a product. A non-exhaustive list of potential organisms include: *Clostridium thermocellum; Clostridium thermohydrosulfuricum*; a variety of *Bacillus* species (i.e., *B. subtilis, B. thermoamylovorans, B. stearothermophilus, B. granulobacter, B. pectinovorum, B. halodurans*, and/or so forth); and/or those described herein. The transpososome HAM constructs may be introduced into the organism by any technique known in the art, such as, but not limited to, electroporation, and so forth. Such techniques are known in the art and are detailed in Sambrook J. C., E. F. Fritsch, and T. Maniatas, 1989. *Molecular Cloning: A Laboratory Manual*, 2nd ed., Cold Spring Harbor Laboratory Press, N.Y, p. 6.3-6.34; or Sambrook and Russell, *Molecular Cloning: A Laboratory Manual* (3-*Volume Set*), $3^{rd}$ ed. (available online at molecularcloning.com/); both references incorporated by reference herein.

Example 2(b): Recombination/Integration of Hydrolysis Associated Molecules into Genome of Organism Able to Ferment Sugar to Ethanol One or more HAMs are integrated into the genome of an organism that is able to ferment and/or convert sugar molecules to a product. A transpososome is made that includes the HAMs and contains sequences for promoting the integration of the included HAM(s) into the genome. The transpososome construct may be any type and/or kind of transpososome construct known in the art, such that the transpososome construct assists in the integration of the one or more HAMs into a host genome. Such transpososome may include Mu based transpososomes or the like.

Example 3: Transformation/Expression of Hydrolysis Associated Molecules and Fermentation Associated Molecules in an Organism Both HAMs and FAMs are expressed in a suitable organism. The HAMs and FAMs to be expressed include any and/or all of the Hydrolysis or Fermentation Associated Molecules as described herein.

Example 3(a): Transformation of Hydrolysis Associated Molecules and Fermentation Associated Molecules Using a Transpososome One or more transpososomes are constructed including HAMs and/or FAMs. Similar to Example 1 and Example 2, included in each of the transpososomes are the nucleic acids necessary for insertion and expression of the nucleic acids in the transpososome. Included in the transpososome are the nucleic acids necessary for insertion of the transposon, copies of the MuA transposase, Mu transposon ends, and provision for expression of the nucleic acids contained in the transpososome in the particular organism in which they are to be utilized. Transpososomes may also be constructed using sequences and elements optimized for use in gram-positive bacteria. See, Pajunen et al., *Microbiology* (2005) 151, 1209-1218. Conventional techniques may be used to construct the transpososome. Additionally, the construction and/or insertion of desired nucleic acids into transpososomes is well known in the art, see, Pajunen et al. It is contemplated that multiple transpososomes may be constructed with the HAMs and FAMs, and may include a variety of promoters and/or enhancers that may function to enhance expression of HAMs and/or FAMs.

Once constructed, the transpososomes are introduced into a target organism. Some non-limiting examples of potential organisms include *E. coli*, any type and/or kind of thermophilic bacteria (e.g., *Sulfolobus, Thermoproteus*, etc.), and/or so forth. The transpososome constructs may be introduced into the organism by any technique known in the art, or as described herein.

Example 3(b): Integration of Hydrolysis and Fermentation Associated Molecules into Genome of Organisms One or more FAMs and/or HAMs are integrated into the genome of *A. acidocaldarius*. A transpososome is made that includes FAMs and/or HAMs and contains sequences for promoting the integration of the included FAMs and/or HAMs into the genome. The transpososome may be any type and/or kind of transpososome construct known in the art, such that the transpososome assists in the integration of the one or more FAMs and/or HAMs into a host genome. Such transpososomes may include Mu based transpososomes or the like.

All references, including publications, patents, and patent applications, cited herein are hereby incorporated by reference to the same extent as if each reference were individually and specifically indicated to be incorporated by reference and were set forth in its entirety herein.

While this invention has been described in certain embodiments, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims and their legal equivalents.

Example 4 RAAC02661: A Xylan Alpha-Glucuronidase

Provided in SEQ ID NO:336 is a nucleotide sequence isolated from *Alicyclobacillus acidocaldarius* and encoding the polypeptide of SEQ ID NO:337. As can be seen in FIGS. 21A-21D, SEQ ID NO:337 aligns well with other proteins identified as xylan alpha-glucuronidases. Of particular importance, it is noted that where amino acids are conserved in other xylan alpha-glucuronidases, those amino acids are generally conserved in SEQ ID NO:337. Thus, the polypeptide provided in SEQ ID NO:337 is properly classified as a xylan alpha-glucuronidase.

The polypeptides of SEQ ID NOs:348-352 are representative examples of conservative substitutions in the polypeptide of SEQ ID NO:337 and are encoded by the nucleotide sequences of SEQ ID NOs:343-347, respectively.

The nucleotide sequences of SEQ ID NOs:336 and 343-347 are placed into expression vectors using techniques standard in the art. The vectors are then provided to cells such as bacteria cells or eukaryotic cells such as Sf9 cells or CHO cells. In conjunction with the normal machinery present in the cells, the vectors comprising SEQ ID NOs:336 and 343-347 produce the polypeptides of SEQ ID NOs:337 and 348-352. The polypeptides of SEQ ID NOs:337 and 348-352 are then isolated and/or purified. The isolated and/or purified polypeptides of SEQ ID NOs:337 and 348-352 are then demonstrated to have activity as xylan alpha-glucuronidases.

The isolated and/or purified polypeptides of SEQ ID NOs:337 and 348-352 are challenged with polysaccharides, lignocellulose, cellulose, hemicellulose, lignin, starch, chitin, polyhydroxybutyrate, heteroxylans, glycosides, xylan-, glucan-, galactan-, and/or mannan-decorating groups. The isolated and/or purified polypeptides of SEQ ID NOs:337 and 348-352 are demonstrated to have activity in at least partially degrading, cleaving, and/or removing polysaccharides, lignocellulose, cellulose, hemicellulose, lignin, starch, chitin, polyhydroxybutyrate, heteroxylans, glycosides, xylan-, glucan-, galactan-, and/or mannan-decorating groups.

Example 4(a) Production and Purification of RAAC02661

The nucleotide sequence of SEQ ID NO:337 was cloned from *Alicyclobacillus acidocaldarius*. SEQ ID NO:336 encodes the polypeptide of SEQ ID NO:337. SEQ ID NO:336 was cloned into the pBAD/HIS A expression vector for *E. coli* and provided to *E. coli* via electroporation. Expression of SEQ ID NO:337 was detected from transformed *E. coli* comprising SEQ ID NO:336 and RAAC02661 was affinity purified using a cobalt resin for activity testing.

Example 4(b) α-glucuronidase (AGUR) Activity of RAAC02661

RAAC02661 purified from *E. coli* was tested for XYL activity using an assay summarized as follows:

A solution of aldouronic acids (AUAs) was created by diluting 50 μL of a mixture of aldotetraouronic acid, aldotriouronic acid and aldobiouronic acid (40:40:20; Aldouronic Acid Mixture, Megazyme Cat. No. O-AMX) with 1.95 mL of an appropriate buffer at 50 mM for pHs ranging from 1 to 9. Buffers included maleic acid (pH 1.0-2.0), Glycine HCl (pH 3.0), sodium acetate (pH 3.5-5.0), sodium phosphate (pH 6.0-8.0), Tris-HCl (pH 9.0), and CAPS buffer (pH 10.0).

Samples of purified RAAC02661 generated in Example 38 were diluted to an appropriate concentration for activity measurement in the appropriate buffer at 50 mM for pHs ranging from 1 to 10. Samples (RAAC02661 samples and positive controls) were placed in the wells of a 96-well plate in 10 μL aliquots. Blanks of buffer only were placed in some wells. AUA solution, preheated to 50, 60, 70, 80, or 90 degrees Celsius, was then added to each well and the plate was incubated at 50, 60, 70, 80, or 90 degrees Celsius for 3 minutes. Dinitrosalicylic acid solution was then added to each well and the plate was further incubated at 80 degrees Celsius for an additional 10 minutes. The AGUR activity was measured using a 96-well plate reader (Molecular Devices UV-Vis) at a wavelength of 540 nm. Specific activity for RAAC02661 as determined appears in FIG. 2.

BIBLIOGRAPHIC REFERENCES

Garrote, G., H. Dominguez, and J. C. Parajo, 2001, Manufacture of xylose-based fermentation media from corncobs by posthydrolysis of autohydrolysis liquors, *Appl. Biochem. Biotechnol.,* 95:195-207.

Hamelinck, C. N., G. van Hooijdonk, and A. P. C. Faaij, 2005, Ethanol from lignocellulosic biomass: techno-economic performance in short-, middle-, and long-term, *Biomass Bioenergy,* 28:384-410.

Laitinen et al., 2005, *A Multipurpose Vector system for the screening of libraries in bacteria, insect and mammalian cells and expression in vivo, Nucleic Acids Research* 33(4).

Liu C., and C. E. Wyman, 2003, The effect of flow rate of compressed hot water on xylan, lignin, and total mass removal from corn stover, *Ind. Eng. Chem. Res.,* 42:5409-5416.

Lynd et al., 2002, *Micro. and Mol. Biol. Rev.,* vol. 66, No. 3, pp. 506-577.

Sambrook J. C., E. F. Fritsch, and T. Maniatas, 1989. *Molecular Cloning: A Laboratory Manual,* 2nd ed., Cold Spring Harbor Laboratory Press, N. Y, pp. 6.3-6.34.

Sambrook and Russell, 2001, *Molecular Cloning: A Laboratory Manual* (3-Volume Set), $3^{rd}$ ed. (available online at molecularcloning.com/).

Ng et al., 1981, *Applied and Environmental Microbiology,* 41(6): 1337-1343.

Tsao, G. T., M. R. Ladisch, and H. R. Bungay, 1987. Biomass Refining, In *Advanced Biochemical Engineering,* Wiley Interscience, N.Y., pp. 79-101.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US10689634B2). An electronic copy of the "Sequence Listing" will also be available from the USPTO upon request and payment of the fee set forth in 37 CFR 1.19(b)(3).

What is claimed is:

1. A genetically modified bacteria or fungus comprising:
   at least one exogenous nucleic acid encoding a polypeptide having at least 90% sequence identity to SEQ ID NO: 304; and
   wherein the polypeptide has carboxylesterase type B activity.

2. The genetically modified bacteria or fungus of claim 1, wherein the at least one exogenous nucleic acid is integrated into the host organism's genome.

3. The genetically modified bacteria or fungus of claim 1, wherein the polypeptide has carboxylesterase type B activity at or above fifty degrees Celsius.

4. The genetically modified bacteria or fungus of claim 1, wherein the polypeptide comprises SEQ ID NO: 304.

5. The genetically modified bacteria or fungus of claim 1, wherein the at least one exogenous nucleic acid has at least 90% homology to SEQ ID NO:303.

6. The genetically modified bacteria or fungus of claim 1, wherein the at least one exogenous nucleic acid is SEQ ID NO:303.

7. An extract isolated from the genetically modified bacteria or fungus of claim 1, wherein the extract comprises the polypeptide having carboxylesterase type B activity and a polypeptide natively produced by the genetically modified organism.

8. A method for at least partially processing hemicellulose into a product, the method comprising:
   contacting a liquid culture medium of the genetically modified bacteria or fungus of claim 1 with hemicellulose, wherein the liquid culture medium comprises the polypeptide having carboxylesterase type B activity.

9. The method according to claim 8, wherein the contacting occurs at or above fifty degrees Celsius.

10. A method for at least partially processing hemicellulose, the method comprising:
    isolating an enzyme extract from the genetically modified bacteria or fungus of claim 1; and
    contacting the extract with hemicellulose,
    wherein the extract comprises the polypeptide having carboxylesterase type B activity and a polypeptide natively produced by the genetically modified organism.

11. A method of producing a product from biomass, the method comprising:

pretreating the biomass with an acid;

enzymatically hydrolyzing cellulose and hemicellulose in the biomass to produce monomeric sugars and concurrently fermenting the monomeric sugars to a product; and recovering the product, wherein at least a portion of the hydrolyzing of cellulose and hemicellulose or the fermentation is performed by the genetically modified bacteria or fungus of claim 1.

12. A method of producing a product from biomass, the method comprising:

pretreating the biomass with an acid;

enzymatically hydrolyzing cellulose and hemicellulose in the biomass to produce monomeric sugars;

fermenting the monomeric sugars to a product; and recovering the product, wherein at least a portion of the hydrolyzing of cellulose and hemicellulose or the fermentation is performed by the genetically modified bacteria or fungus according to claim 1, and wherein the pretreatment, the hydrolyzing of cellulose and hemicellulose, and the fermentation are performed concurrently.

13. A method of processing biomass, the method comprising:

treating the biomass with an acid and concurrently enzymatically hydrolyzing cellulose and hemicellulose in the biomass to produce monomeric sugars, wherein at least a portion of the hydrolyzing of cellulose and hemicellulose is performed by the genetically modified bacteria or fungus of claim 1.

14. The genetically modified bacteria or fungus of claim 1, wherein the exogenous nucleic acid is contained in a vector.

* * * * *